(12) United States Patent
Fleckenstein

(10) Patent No.: US 8,323,668 B2
(45) Date of Patent: Dec. 4, 2012

(54) PREVENTION AND TREATMENT OF GRAM NEGATIVE, FLAGELLATED BACTERIAL INFECTIONS

(75) Inventor: James M. Fleckenstein, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 1288 days.

(21) Appl. No.: 12/079,304

(22) Filed: Mar. 26, 2008

(65) Prior Publication Data

US 2011/0206694 A1     Aug. 25, 2011

Related U.S. Application Data

(60) Provisional application No. 60/920,065, filed on Mar. 26, 2007.

(51) Int. Cl.
| | |
|---|---|
| *A61K 39/108* | (2006.01) |
| *A61K 39/00* | (2006.01) |
| *A61K 39/395* | (2006.01) |
| *A61K 45/00* | (2006.01) |
| *A61K 39/40* | (2006.01) |

(52) U.S. Cl. ............... 424/257.1; 424/192.1; 424/130.1; 424/278.1; 424/241.1; 424/169.1; 424/184.1

(58) Field of Classification Search .................. None
See application file for complete search history.

(56) References Cited

U.S. PATENT DOCUMENTS

| 6,987,176 B1 * | 1/2006 | Guerry et al. ................ 536/23.1 |
| 2002/0161192 A1 * | 10/2002 | Meyer et al. .................. 530/350 |
| 2011/0117128 A1 * | 5/2011 | Powell et al. ............. 424/210.1 |

OTHER PUBLICATIONS

Bowie et al. (Science, 1990, 257:1306-1310).*
Fleckenstein et al., Infection and Immunity, 2006; 74(4): 2245-2258.*
Brown et al., Mol Gen Genomics, 2004; 272: 201-215.*

* cited by examiner

*Primary Examiner* — Gary Nickol
*Assistant Examiner* — Lakia Tongue
(74) *Attorney, Agent, or Firm* — Benjamin Aaron Adler

(57) ABSTRACT

The present invention describes a novel mechanism of adhesion by flagellated Gram-negative bacteria such as enterotoxigenic *Escherichia coli* (ETEC), where the bacteria secretes a protein, EtpA which binds to the conserved region of the flagellin protein located at the tip of the flagella. The present invention also discloses that EtpA-mediated interaction and intestinal colonization require interaction with flagellin. Also disclosed herein is a vaccine composition that can be used for either active or passive immunization of mammals for the prevention or treatment of infections caused by flagellated Gram-negative bacteria.

9 Claims, 16 Drawing Sheets

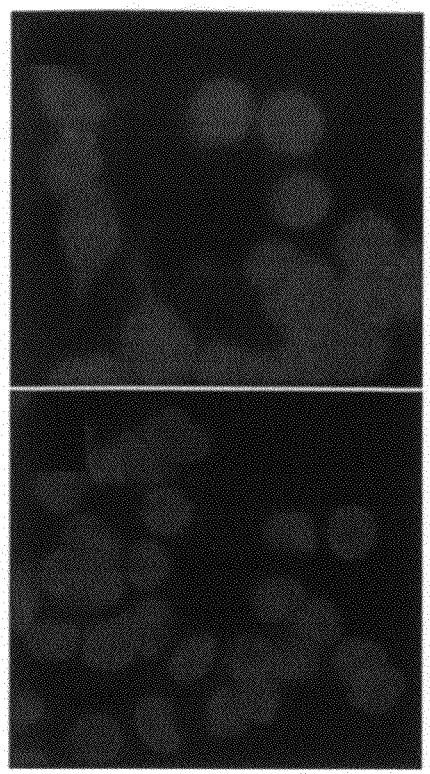
Fig. 2A
Fig. 2B
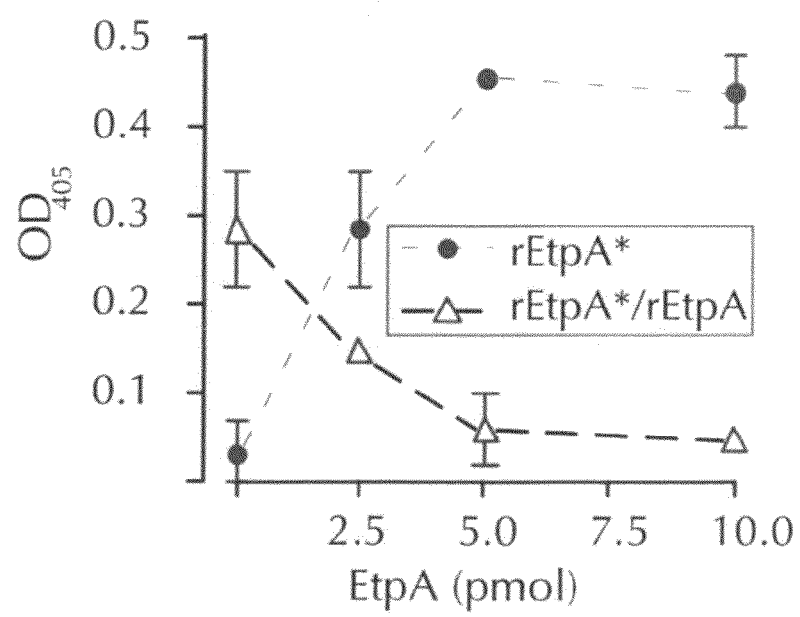
Fig. 2C

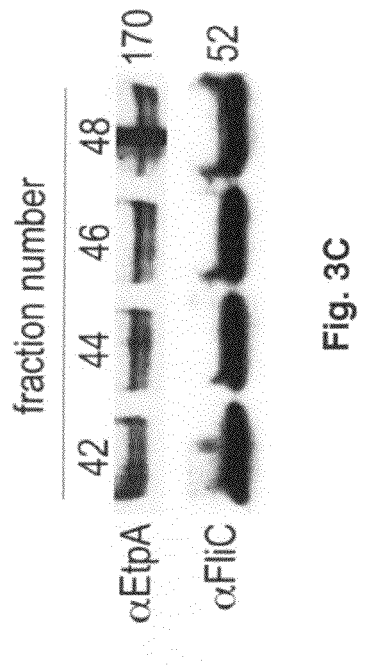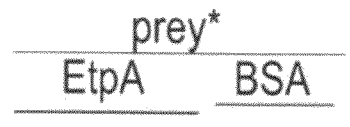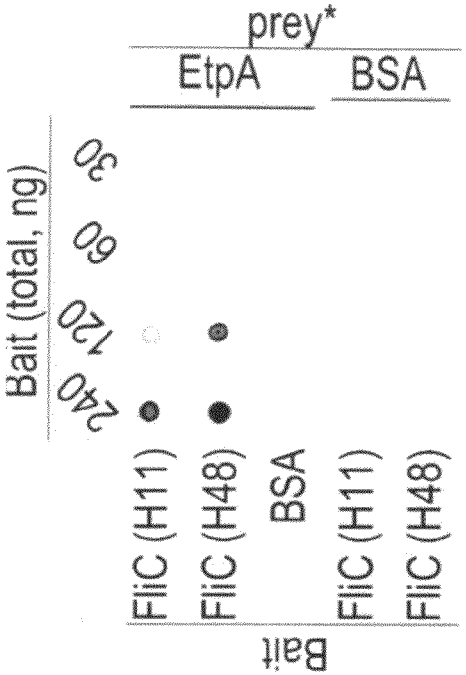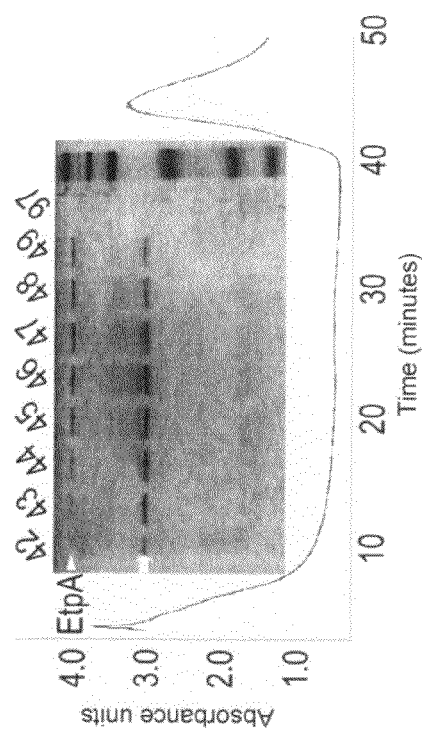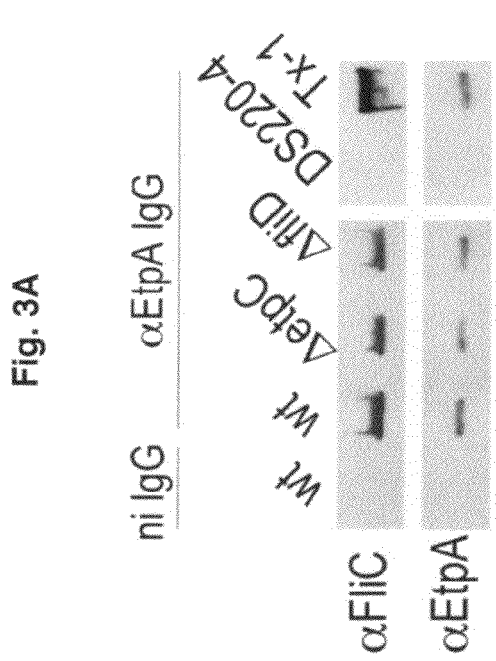

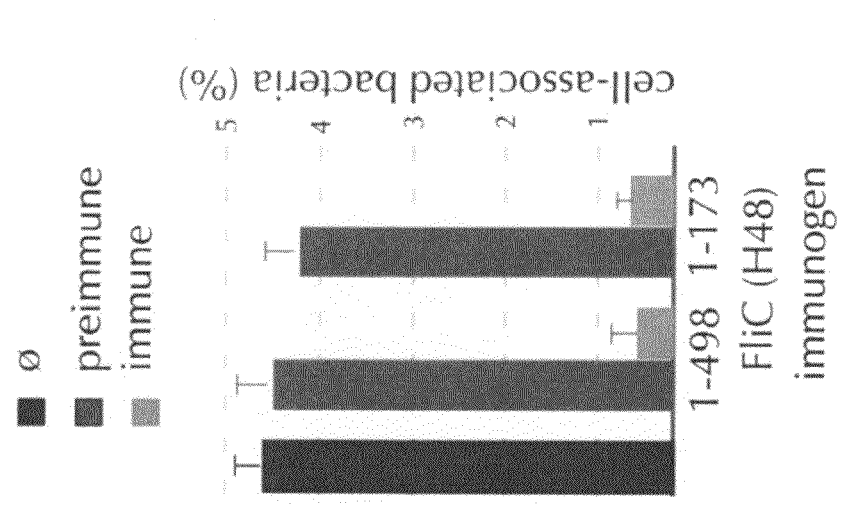
Fig. 4D
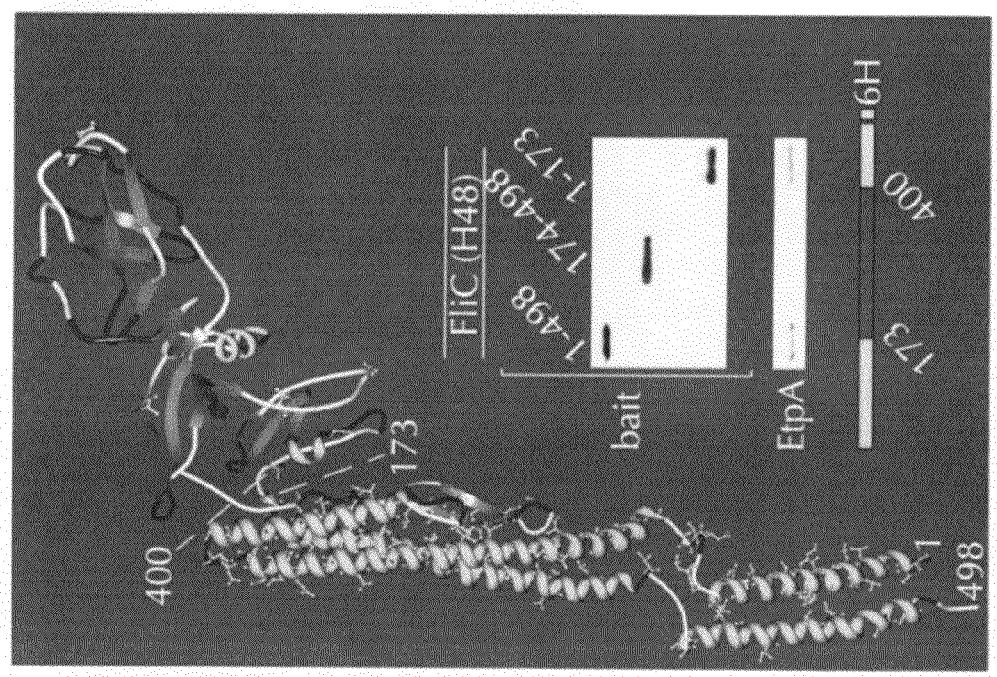
Fig. 4C
Fig. 4B

Fig. 5G        Fig. 5H

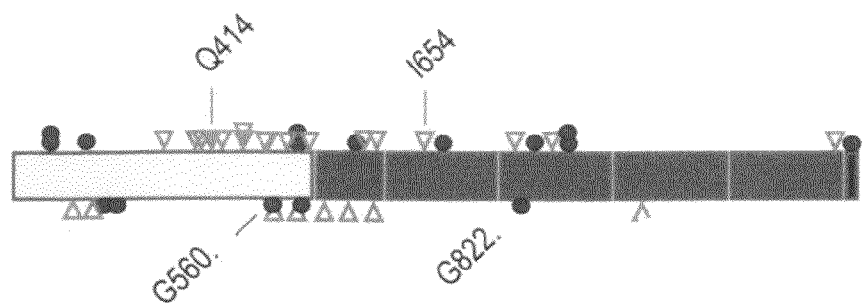
Fig. 6A
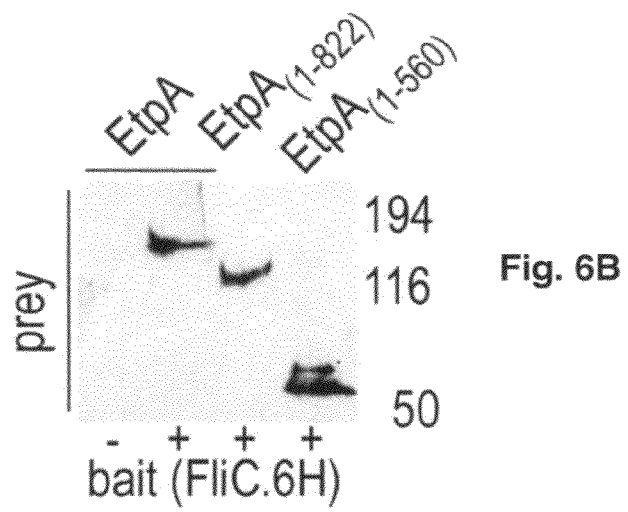
Fig. 6B
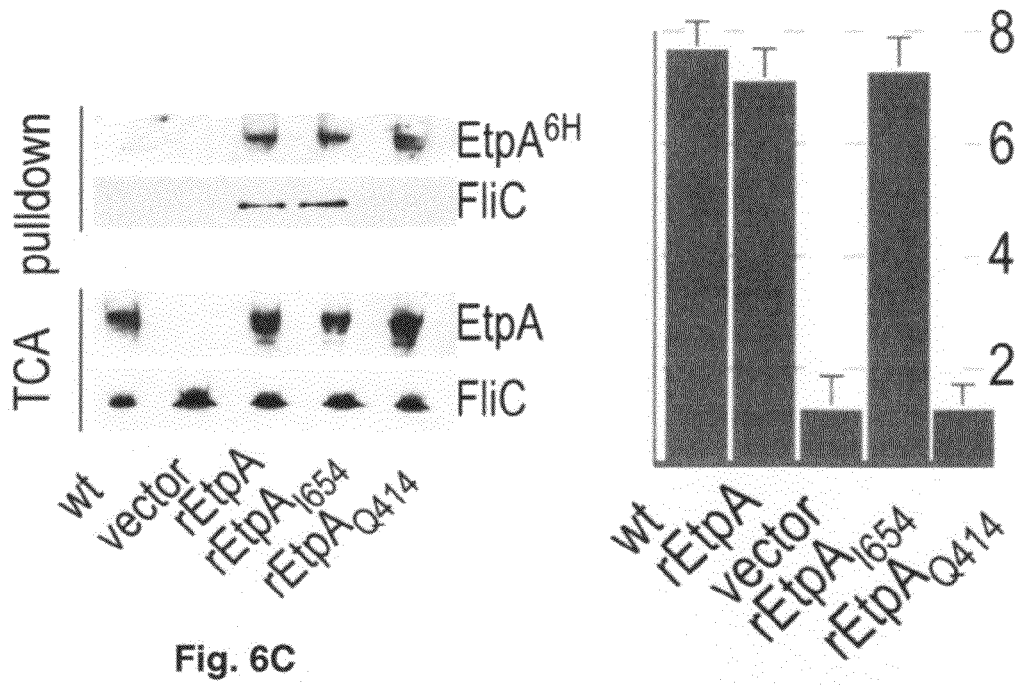
Fig. 6C
Fig. 6D

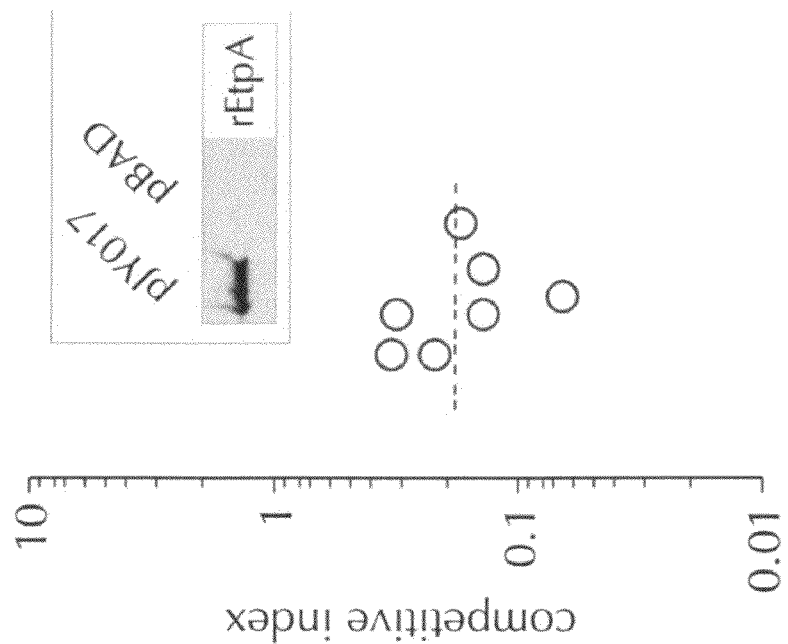
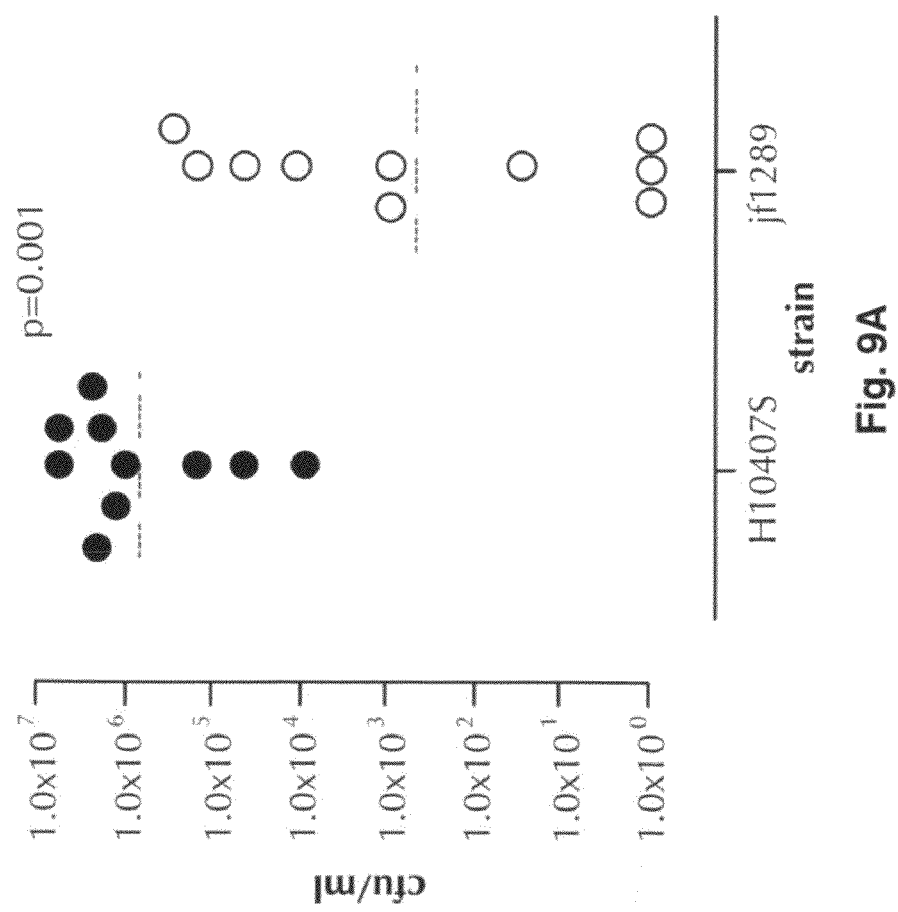
Fig. 9B
Fig. 9A

SEQUENCE LISTING

<160> NUMBER OF SEQ ID NOS: 16

<210> SEQ ID NO 1
<211> LENGTH: 67
<212> TYPE: DNA
<213> ORGANISM: artificial sequence
<220> FEATURE:
<221> NAME/KEY: primer_binding
<223> OTHER INFORMATION: jf121905.1 primer

<400> SEQUENCE: 1
ggaaacccaa tacgtaatca acgacttgca atataggata acgaatcgtg            50
taggctggag ctgcttc                                                67

<210> SEQ ID NO 2
<211> LENGTH: 64
<212> TYPE: DNA
<213> ORGANISM: artificial sequence
<220> FEATURE:
<221> NAME/KEY: primer_binding
<223> OTHER INFORMATION: jf121905.2 primer

<400> SEQUENCE: 2
tgccaacacg gagttaccgg cctgctggat gatctgcgct ttcgacatat            50
gaatatcctc ctta                                                   64

<210> SEQ ID NO 3
<211> LENGTH: 33
<212> TYPE: DNA
<213> ORGANISM: artificial sequence
<220> FEATURE:
<221> NAME/KEY: primer_binding
<223> OTHER INFORMATION: jf011706.1 primer

<400> SEQUENCE: 3
aataataagc ttatggcaca agtcattaat acc                              33

<210> SEQ ID NO 4
<211> LENGTH: 30
<212> TYPE: DNA
<213> ORGANISM: artificial sequence
<220> FEATURE:
<221> NAME/KEY: primer_binding
<223> OTHER INFORMATION: jf011706.2 primer

<400> SEQUENCE: 4
aataatagat ctttaaccct gcagcagaga                                  30

<210> SEQ ID NO 5
<211> LENGTH: 31
<212> TYPE: DNA
<213> ORGANISM: artificial sequence
<220> FEATURE:
<221> NAME/KEY: primer_binding
<223> OTHER INFORMATION: jf031505.1 primer

<400> SEQUENCE: 5
aataatctcg agaatggtgg tgaaattcat g                                31

<210> SEQ ID NO 6
<211> LENGTH: 30
<212> TYPE: DNA
<213> ORGANISM: artificial sequence
<220> FEATURE:
<221> NAME/KEY: primer_binding

```
<223> OTHER INFORMATION: jf110705.2 primer

<400> SEQUENCE: 6
aataataagc ttttgccagt acacctcact                                    30

<210> SEQ ID NO 7
<211> LENGTH: 37
<212> TYPE: DNA
<213> ORGANISM: artificial sequence
<220> FEATURE:
<221> NAME/KEY: primer_binding
<223> OTHER INFORMATION: jf071706.1 primer

<400> SEQUENCE: 7
catcatcatc attgagttca aacggtctcc agcttgg                            37

<210> SEQ ID NO 8
<211> LENGTH: 37
<212> TYPE: DNA
<213> ORGANISM: artificial sequence
<220> FEATURE:
<221> NAME/KEY: primer_binding
<223> OTHER INFORMATION: jf071706.2 primer

<400> SEQUENCE: 8
ccaagctgga gaccgtttga actcaatgat gatgatg                            37

<210> SEQ ID NO 9
<211> LENGTH: 30
<212> TYPE: DNA
<213> ORGANISM: artificial sequence
<220> FEATURE:
<221> NAME/KEY: primer_binding
<223> OTHER INFORMATION: primer N

<400> SEQUENCE: 9
actttattgt catagtttag atctattttg                                    30

<210> SEQ ID NO 10
<211> LENGTH: 30
<212> TYPE: DNA
<213> ORGANISM: artificial sequence
<220> FEATURE:
<221> NAME/KEY: primer_binding
<223> OTHER INFORMATION: primer S

<400> SEQUENCE: 10
ataatcctta aaaactccat ttccacccct                                    30

<210> SEQ ID NO 11
<211> LENGTH: 18
<212> TYPE: DNA
<213> ORGANISM: artificial sequence
<220> FEATURE:
<221> NAME/KEY: primer_binding
<223> OTHER INFORMATION: jf092605.3 primer

<400> SEQUENCE: 11
cagattgtgg caggttca                                                 18

<210> SEQ ID NO 12
<211> LENGTH: 21
<212> TYPE: DNA
<213> ORGANISM: artificial sequence
<220> FEATURE:
<221> NAME/KEY: primer_binding
<223> OTHER INFORMATION: jf122205.1 primer
```

```
-continued

<400> SEQUENCE: 12
ctaaaacaga atcccgctat c                                              21

<210> SEQ ID NO 13
<211> LENGTH: 33
<212> TYPE: DNA
<213> ORGANISM: artificial sequence
<220> FEATURE:
<221> NAME/KEY: primer_binding
<223> OTHER INFORMATION: jf030106.1 primer

<400> SEQUENCE: 13
aataatagat ctatggcaca agtcattaat acc                                 33

<210> SEQ ID NO 14
<211> LENGTH: 34
<212> TYPE: DNA
<213> ORGANISM: artificial sequence
<220> FEATURE:
<221> NAME/KEY: primer_binding
<223> OTHER INFORMATION: jf030106.2 primer

<400> SEQUENCE: 14
aataataagc tttaccctgc agcagagaca gaac                                34

<210> SEQ ID NO 15
<211> LENGTH: 33
<212> TYPE: DNA
<213> ORGANISM: artificial sequence
<220> FEATURE:
<221> NAME/KEY: primer_binding
<223> OTHER INFORMATION: jf050206.1 primer

<400> SEQUENCE: 15
aataatagat ctagcgttaa aaataacgat aca                                 33

<210> SEQ ID NO 16
<211> LENGTH: 34
<212> TYPE: DNA
<213> ORGANISM: artificial sequence
<220> FEATURE:
<221> NAME/KEY: primer_binding
<223> OTHER INFORMATION: jf050206.2 primer

<400> SEQUENCE: 16
aataataagc tttaaaacca tcaaggccaa gagt                                34
```

PREVENTION AND TREATMENT OF GRAM NEGATIVE, FLAGELLATED BACTERIAL INFECTIONS

CROSS REFERENCE TO RELATED APPLICATION

This non-provisional application claims benefit of provisional application U.S. Ser. No. 60/920,065 filed on Mar. 26, 2007, now abandoned.

FEDERAL FUNDING LEGEND

This invention was produced using funds obtained through grant RR-16190-05 from the National Institutes of Health, and Merit Review Funding from the Department of Veterans Affairs. Consequently, the Federal government has certain rights in this invention.

BACKGROUND OF THE INVENTION

1. Field of the Invention

The present invention relates generally to the field of microbiology, immunology and vaccine development. More specifically, the present invention discloses flagellin and secreted two-partner secretion proteins as target antigens in the development of vaccines for flagellated human pathogens such as enterotoxigenic *escherichia coli* (ETEC).

2. Description of the Related Art

Infectious diarrhea is a leading cause of mortality in developing countries accounting for more than one fifth of all deaths under the age of 5 years (Kosek et al., 2003). In this population, enterotoxigenic *Escherichia coli* (ETEC) commonly cause diarrhea with annual estimates of diarrheal illness approaching one billion episodes (WHO, 2006), resulting in hundreds of thousands of deaths. Enterotoxigenic *Escherichia coli* cause an estimated 500,000 deaths per year in young children and are perenially the most common causes of diarrheal illness in travellers (Sack, 1990; Jiang et al., 2002) and soldiers deployed to developing countries (Hyams et al., 1991; Bourgeois et al., 1993). Enterotoxigenic *Escherichia coli* have also emerged in several recent large-scale outbreaks in the United States (Beatty et al., 2006; Daniels, 2006).

Illness caused by ETEC may range from mildly symptomatic to severe, life-threatening cholera-like diarrhea (Sack et al., 1971; Vicente et al., 2005). In the classic paradigm for enterotoxigenic *Escherichia coli* pathogenesis, these organisms utilize fimbrial colonization factors (CFs) to colonize the intestine where they elaborate heat labile (LT) and/or heat stable (ST) enterotoxins that elicit watery diarrhera.

Painstaking ETEC vaccine development efforts, which have largely targeted colonization factors (CFs) (Boedeker, 2005), have been hindered by the fact that these antigens are neither cross-protective nor well-conserved, and in some cases identified only in a minority of strains even after diligent searches for more than 20 colonization factors that have been discovered to date (Peruski et al., 1999). Similarly, the toxins produced by enterotoxigenic *Escherichia coli* are either poorly immunogenic in the case of the heat stable toxin (ST) or appear to offer limited protection despite robust antigenicity in the case of the cholera toxin-like heat labile toxin (LT) (Clemens et al., 1988). This later phenomenon may be explained by the ability of enterotoxigenic *Escherichia coli* to deliver its toxin payload in a fashion that circumvents immune neutralization (Dorsey et al., 2006).

Recently EtpA, identified in a search for novel ETEC antigens (Fleckenstein et al., 2006) is a large glycoprotein secreted by the prototypical enterotoxigenic *Escherichia coli* H10407 strain that was originally isolated from a patient in Bangladesh with severe cholera-like diarrheal illness (Evans et al., 1975). EtpA is a member of a large family of potential virulence proteins that are secreted by two-partner secretion (TPS) systems (Jacob-Dubuisson et al., 2001). In two-partner secretion systems, one partner (generically referred to as TpsB proteins) transports a second secreted (TpsA) protein through the bacterial outer membrane. Although EtpA, like other TPS exoproteins, promotes adhesion to epithelial cells, its precise mechanism is not clear.

Furthermore, many other elements of the pathogenesis of enterotoxigenic *Escherichia coli* remain poorly understood. One aspect that has not been sufficiently explored is the role played by flagella. *E. coli* are serotyoed based on their lipopolysaccharide (O) and flagellar (H) antigens, and enterotoxigenic *Escherichia coli* flagella have largely been relegated to serotyping with virtually no investigation of a role in pathogenesis (Wolf, 1997). However, flagellar organelles from a number of Gram-negative pathogens play critical roles in pathogenesis by promoting adherence to epithelial cells (Giron et al., 2002; Yao et al., 1994), formation of biofilms (Pratt and Kolter, 1998) and colonization (Wright et al., 2005; Lane et al., 2005; Correa et al., 2000). It has also been recently demonstrated that production of intact flagella and motility are essential for the successful delivery of heat-labile enterotoxin to epithelial cells by enterotoxigenic *Escherichia coli* (Dorsey et al., 2006).

Flagella are complex extracellular structures each composed of approximately 20,000 molecules of the protein flagellin (FliC) arranged in a cylindrical lattice of 11 helical protofilaments. The FliC monomer is thought to travel down the nascent cylinder in an unfolded state to the distal end (tip) where the flagellar cap protein, FliD (Yonekura et al., 2000), directs assembly of flagellin monomers into the growing flagellum. Flagellin has several major domains: the central variable domain projects outward along the surface of the flagellar shaft and accounts for the antigenic variation on which the "H" serotyping is based; conserved amino and carboxy terminal regions participate in interactions between individual subunits and face the inaccessible inner core of the flagellar shaft once incorporated into the cylinder (Yonekura et al., 2003).

Thus, prior art lacks complete understanding of the pathogenesis of enterotoxigenic *Escherichia coli* and is deficient in the knowledge of antigens of enterotoxigenic *Escherichia coli* that can be targeted to prevent enterotoxigenic *Escherichia coli* infection. The current invention fulfils this long-standing need in the art.

SUMMARY OF THE INVENTION

In one embodiment of the present invention, there is provided an immunogenic composition comprising a two-partner secretion protein(s), a flagellin protein or fragments thereof, a pharmaceutically acceptable adjuvant or a combination thereof.

In a related embodiment of the present invention, there is provided a method of preventing an infection caused by a flagellated Gram-negative bacteria in an individual. This method comprises administering an immunologically effective amount of the immunogenic composition comprising the two-partner secretion protein(s), the flagellin protein or the fragments thereof, the pharmaceutically acceptable adjuvant or the combination thereof to the individual.

In another embodiment of the present invention, there is provided an antibody directed against one or more of two-partner secretion protein(s), a flagellin protein or fragments thereof. In a related embodiment of the present invention, there is provided a method of treating an infection caused by a flagellated Gram-negative bacteria in the individual. Such a method comprises administering an immunologically effective amount of the antibody directed against one or more of two-partner secretion protein(s), the flagellin protein or the fragments thereof to the individual, thereby treating the infection caused by the flagellated Gram-negative bacteria in the individual.

In yet another embodiment of the present invention, there is provided a method of preventing diarrhea caused by the Enterotoxigenic *Escherichia coli* in an individual. Such a method comprises administering an immunogenic composition comprising EtpA or a full-length flagellin or flagellin subunit derivatives containing the highly conserved regions of flagellin molecules such as those found in *E. coli* flagellin serotype H48, wherein the highly conserved regions of flagellins are amino acids 1-173 or 400-498 to an individual.

BRIEF DESCRIPTION OF THE DRAWINGS

The appended drawings have been included herein so that the above-recited features, advantages and objects of the invention will become clear in detail. These drawings form a part of the specification. It is to be noted, however, that the appended drawings illustrate preferred embodiments of the invention and should not be considered to limit the scope of the invention.

FIG. 1A shows that EtpA and production of intact flagella are required for adherence. Results demonstrate adherence of wild type ETEC strain H10407 (wt), the etpA mutant (jf1289), the flic mutant (jf1412) or the fliD mutant (jf721) added to CaCo-2 cells. Asterisks (*) reflect P values=0.0286 obtained by Mann-Whitney test comparison (bars represent the mean±standard deviation for n=4 replicates for each experiment). FIG. 1B shows that adherence is not dependent on flagellar serotype. Complementation of the fliC (H11⁻) isogenic deletion strain jf1412 with plasmid pJY044 expressing the fliC gene from MG1655 (*E. coli* K-12, flagellar serotype H48) restores motility and adherence phenotypes. Soft agar motility assays for WT, jf1412, jf1412 (pFLAG) and jf1412(pJY044), respectfully, are shown. FIG. 1C shows that affinity-purified antibodies against flagellin (H48) inhibit ETEC H10407 (O78:H11) adherence to intestinal epithelial cells. (nrs=normal preimmune rabbit sera). FIG. 1D shows that anti-EtpA antisera inhibits adherence of multiple motile EtpA-producing ETEC strains H10407 (CFAI, O78:H11), DS61-1 (CFAII, O6:H16) and Tx-1 (CFAI, O78:H12). Relative amounts of EtpA produced by the respective strains are indicated in the anti-EtpA immunoblot (inset). [densitometry measurements by Image J: H10407=61445, DS61-1=5957, Tx-1=33863]. Flagellin (FliC) is shown here as a loading control. FIG. 1E shows that addition of exogenous rEtpA to etpA mutant restores adherence in dose-dependent fashion.

FIGS. 2A-2C show that EtpA interacts with host cell surface molecules. FIG. 2A shows recombinant EtpA (rEtpA) bound to the surface of HCT-8 intestinal epithelial cells following incubation of cells with concentrated culture supernatants from EtpA-expressing Top10(pJY019). FIG. 2B shows same cell line incubated with culture supernatants from vector control strain Top10(pBADmycHisA). FIG. 2C shows binding of purified rEtpA by incubation of target Caco-2 epithelial cells with increasing concentrations of biotinylated protein in the absence of unlabeled inhibitor. Next, increasing concentrations of unlabeled rEtpA ("rEtpA", open triangles) was used in competitive inhibition studies with 2.5 pmol of labeled protein (rEtpA*/rEtpA). Binding of biotinylated protein was then detected using streptavidin-HRP.

FIGS. 3A-3E shows that EtpA interacts with multiple monomeric flagellins. FIG. 3A shows co-purification via high resolution gel filtration column chromatography of EtpA (arrowhead) and second (≈50 kDa) protein (arrow) from supernatant of recombinant *E. coli* (H48) expressing the ETEC etpBAC TPS locus (Dorsey et al., 2006). FIG. 3B shows MALDI-TOF identification of 50 kDa band as flagellin (H48). FIG. 3C shows immunoblots of gel filtration-purified H10407 (O78:H11) supernatants showing co-purification of EtpA with FliC (H11). FIG. 3D shows co-immunoprecipitation of EtpA and $FliC_{H11}$ from ETEC culture supernatants using anti-EtpA antibody. αEtpA IgG=immune antibody; ni IgG=purified non-immune IgG (same rabbit). Shown from left to right are results from the wt (H10407); the etpC mutant; fliD mutant which cannot assemble intact flagella; culture supernatants from other motile ETEC strains (DS220-4; O11: H33; EtpA⁻); (TX-1: O78:H12; EtpA⁺). FIG. 3E shows the interaction of membrane-immobilized $FliC_{H11}$ and $FliC_{H48}$ (bait) with biotinylated rEtpA ("prey*").

FIGS. 4A-4D show that EtpA mimics and interacts with conserved regions of flagellin. FIG. 4A shows similarity between EtpA (line 1) and flagellins identified in EtpA PSI-BLAST (Altschul et al., 1997) searches illustrated by partial ClustalW (Chenna et al., 2003) alignment. (additional EtpA residues are in the parentheses). Numbers (black background) refer to amino acid position in EtpA; blue background *E. coli* MG1655H48 flagellin. Different *E. coli* H serotypes are shaded yellow. FIG. 4B shows Protein Workshop (Moreland et al., 2005)-generated image using Protein Data Bank file 1UCU (Yonekura et al., 2003) depicting regions of EtpA homology (amino acid residues in yellow) projected onto flagellin molecule. FIG. 4C shows interaction of EtpA with a conserved region of flagellin. Immunoblots (anti-flagella, top; anti-EtpA, bottom) represent molecular pull-down experiments using recombinant polyhistidine-tagged FliC H48-based molecules as bait. Schematic at bottom of figure depicts full-length recombinant flagellin from serotype H48. Conserved regions (green), serotype-dependent domains (blue) are shown. FIG. 4D shows antibodies against conserved regions of flagellin (H48) block adherence of ETEC strain H10407 (H11) to Caco-2 epithelial cells.

FIGS. 5A-5I show that interactions between highly conserved regions of flagellin and EtpA occur at the tips of ETEC flagella. FIGS. 5A-5C show in situ immunolocalization of conserved regions of flagellin at the tips of H10407 (O78: H11) flagella using: FIG. 5A, antisera directed against H48 flagella, affinity purified against full-length recombinant $FliC_{H48}$; FIG. 5B, FIG. 5C: affinity-purified antisera specifically generated against the highly conserved N-terminal 173 amino acids of H48 flagellin. FIGS. 5D-5F show immunogold localization of EtpA concentrated at the flagellar tips (white arrowhea) of motile EtpA-producing strains: FIG. 5D, H10407 (O78:H11); FIG. 5E, DS61-1 (O6:H16) and FIG. 5F, TX-1 (O78: H12). FIGS. 5G-5I show that EtpA binds exclusively to conserved regions of flagellin at flagellar tips. In FIGS. 5G and 5H, control anti-EtpA immunogold labeling of TEM grid containing motile FliC+, EtpA−, ETEC strain DS220-4 demonstrates limited background binding to grid (white arrowhead), but not flagellar tips (black arrowheads). FIG. 5I shows molecular pull-down assays using tagged versions of the flagellar cap protein (rFliD-FLAG) and EtpA (rEtpA$^{6H}$). Pull down studies using anti-FLAG (M2) agarose beads are shown at left and those using Co$^{2+}$ metal affinity (Talon) beads are on the right. The last lane of each blot contains 10% of the amount of the respective prey protein used in the pull-down experiments.

FIGS. 6A-6F show that adherence of enterotoxigenic *Escherichia coli* ETEC to epithelial cells in vitro and small intestine colonization require the interaction of EtpA and flagellin. In FIG. 6A, Map of EtpA (repeat regions in blue) showing location of linker scanning mutations (red circles=premature stop codons; green triangles=in-frame insertions). Locations indicated above and below map. FIG. 6B shows molecular pull-downs using (H48) polyhistidine-tagged flagellin (FliC.6H) as bait for full-length rEtpA or truncated versions of rEtpA (M1-G$_{822}$ and M1-G$_{560}$). FIG. 6C shows FliC pull-down using bait polyhistidine-tagged rEtpA or variants containing in-frame linker insertions at the positions indicated. FIG. 6D shows adherence of WT (H10407) of isogenic etpA mutant(jf1668) complemented with expression plasmids for EtpA (pJL017), vector control (pBADmycHisA), EtpA with linker insertions starting at 1654 (pJMF1078) or Q414 (pJMF1087) to target Caco-2 cells. FIG. 6E shows addition of exogenous rEtpA, but not rEtpA$_{Q414}$ complements the adherence defect in the etpA mutant. SDS-PAGE above the graph shows rEtpA(6H) and rEtpA$_{Q414}$(6H) used in assays. (numbers in graph key represent final nm concentrations. FIG. 6F shows murine intestinal colonization competition assay between jf1668(pJL017) and jf1668(pJMF1087). Graph shows the average number of cfu from which either the wild type allele (carried on pJL017) or mutant allele (carried on pJMF1087) were recovered following challenge with 1×10$^4$ cfu of both strains. p=0.0027 (two tailed Mann-Whitney test).

FIG. 7A shows motile ETEC bacteria out-compete flagellin-negative mutant (horizontal line indicates geometric mean colonization index≈0.33). FIG. 7B shows kinetic ELISA data that demonstrates that mice immunized with H48 flagellin recognize conserved regions of H48 and H11. FIG. 7C shows that antisera from mice immunized with H48 recognize the tips of ETEC H10407 (H11) flagella. FIG. 7D shows that vaccination with FliC (H48) flagellin protects against colonization with ETEC H10407 expressing FliC (H11) by targeting conserved regions of flagellin. FIG. 7E shows the total fecal antibody response to conserved regions of flagellin following intransal vaccination with recombinant FliC$_{H48(1-498)}$.

FIG. 8A shows mouse inoculations and challenge timeline. Mice were inoculated with≈1×10$^7$ cfu of either avirulent strain AAEC191A (open triangles) or ETEC prototype strain H10407 (closed triangles) on days 0, 14, 68. Sera, and stool were collected on days 0 and 95 prior to challenge, and samples were frozen at −80° C. for subsequent ELISA. FIG. 8B shows ELISA determination of total serum antibody to EtpA or EtpB following repeated inoculation with AAEC191A (open circles) or H10407 (closed circles). ELISA values represent net increases in OD$_{450}$ from pre- to post-immune. (**p=0.014, *p=0.047) FIG. 8C shows ELISA of fecal antibody responses to EtpA (p=0.012) and EtpB (p=0.012). FIG. 8D shows mouse challenge. Both groups of mice [those previously inoculated with H10407 (closed circles) or AAEC191A (open circles)] were challenged with H10407 at two different doses, 6×10$^7$ cfu and 6×10$^3$ cfu. After 24 hours, mice were sacrificed and the degree of ileal colonization was determined by plate counting. (*p=0.029, and p=0.016 for 10$^7$ and 10$^3$ challenge groups respectively, by two tailed Mann-Whitney test).

FIGS. 9A-9B show that EtpA promotes colonization of murine small intestine. In FIG. 9A, mice pretreated with cimetidine and streptomycin were challenged with WT ETEC (H10407S) or an isogenic etpA deletion mutant (jf1289). Innoculum as determined by serial dilution and plate counting was 8.8×10$^2$ cfu/inoculum (WT) and 9.4×10$^2$ cf/inoculum (etpA). FIG. 9B shows results from competition experiments between etpA mutantjf1668 omplemented with either pBADmyc-HisA (pBAD vector control) or EtpA expression plasmid pJY017.

FIG. 10A shows anti-EtpA responses (ELISA) in serum obtained on day 63 prior to challenge. Control sera have been diluted 1:50; IVX908/rEtpA were diluted 1:1028. (p<0.0001, two-tailed Mann-Whitney) FIG. 10B shows anti-EtpA antibody titers in mice vaccinated with either IVX908 or IVX908/rEtpA. FIG. 10C shows ELISA data for salivary antibody from mice immunized with either IVX908 or IVX908/rEtpA. FIG. 10D shows enterotoxigenic *Escherichia coli* H10407 recovered from small intestine following challenge of mice vaccinated with either IVX908 or IVX908/rEtpA (p=0.0051 by one-tailed Mann-Whitney). Bacteria were recovered from small intestine as described (Allen et al., 2006).

DETAILED DESCRIPTION OF THE INVENTION

Figure 1A:
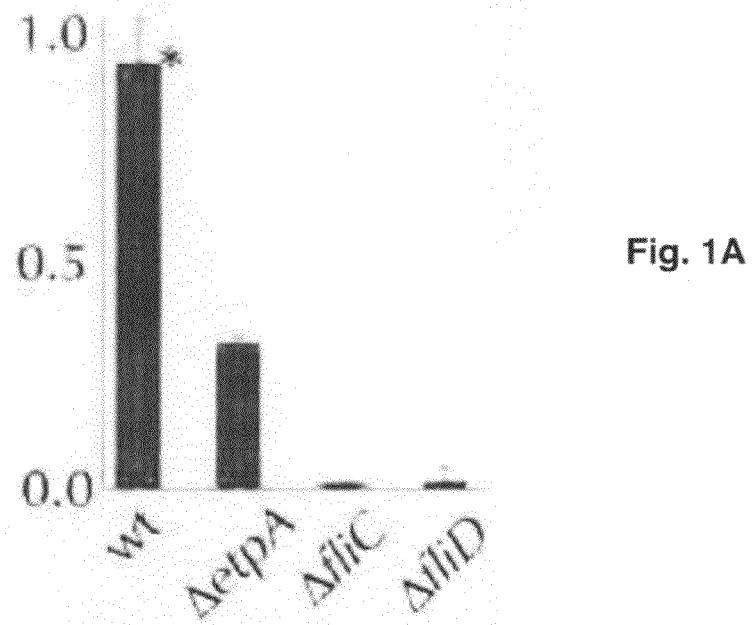
FIGS. 1A-1E show the role of EtpA and flagella in ETEC adherence.

The present invention is directed to identifying immunogenic composition(s) that can be used as vaccine(s) in the prevention and/or treatment of infections caused by enterotoxigenic *Escherichia coli*. In this regard, the present invention describes a novel mechanism of bacterial adhesion by enterotoxigenic *Escherichia coli* in which a recently identified secreted protein, EtpA, binds to the conserved regions of the flagellin protein located at the tips of flagella. The present invention demonstrates that EtpA and the protein that it interacts with, flagellin are viable targets in the development of vaccine for enterotoxigenic *Escherichia coli*.

As discussed supra, the present invention demonstrates for the first time that a bacterial pathogen secretes a virulence protein (EtpA) which interacts specifically with flagellin, and which uses the extended flagellar organelle to present the anchored adhesin to host cell surface receptors. It is also demonstrated herein that EtpA interacts with conserved regions of flagellin exposed at the tips of the flagella prior to polymerization of the subunits into the shaft. This concept is consistent with existing models of flagellar assembly where new flagellin monomers are added to the distal end of these organelles (Yonekura et al., 2000; Yonekura et al., 2003), while only the central serotype-specific regions of flagellin are exposed along the shaft of the flagella. Previous studies also suggest that some flagellin secreted via the flagellar export apparatus may not be incorporated into flagella even in the presence of the FliD cap protein and that flagella "leak" monomeric flagellin (Komoriya et al., 1999). The demonstration that conserved domains of flagellin are exposed and participate in adhesion, represents a significant departure from the prior art. It was previously assumed that these regions were inaccessibly buried within the shaft of the flagella. These new studies provide a molecular basis for previous observations (Giron et al., 2002; Yao et al., 1994) implicating flagella in adherence of other flagellated Gram-negative pathogens. Given the fact that many EtpA-like putative adhesins have been identified through large-scale microbial genome sequencing efforts (Jacob-Dubuisson et al., 2001), other flagellated pathogens may use a similar strategy for adhesion.

Adhesion to host tissues is critical in the pathogenesis of bacterial infections of mucosal surfaces (Ofek et al., 2003), including those caused by enterotoxigenic *Escherichia coli*. Upon colonization of the small intestine enterotoxigenic *Escherichia coli* elaborate enterotoxins causing diarrhea. Previous in vitro studies have suggested that flagella are essential for the process of toxin delivery (Dorsey et al., 2006). The studies presented herein suggest that these structures also play a critical role in adherence and colonization of the small intestine by exposing highly conserved regions of flagellin at the tips of these organelles where they anchor the EtpA adhesin. Therefore, flagella may not simply be required for locomotion. Rather the data presented herein suggest that some bacteria including ETEC may have adapted these rather long (10-15 µm) appendages to tether organisms in their initial encounters with the host cell.

Thus, the findings described herein offer a novel paradigm for the study of bacterial adhesion and explore a phenomenon that could have important implications for the development of vaccines against a variety of Gram-negative pathogens including enterotoxigenic *Escherichia coli*. Interestingly, recent clinical trials suggest that vaccination with flagella can prevent infection with the Gram-negative pathogen, *pseudomonas* (Doring et al., 2007). It should be noted that in these studies multiple serotypes of flagellin were employed. Flagella have previously been dismissed in development of enterotoxigenic *Escherichia coli* vaccines due to the substantial variation in the serotype determinant regions of the flagellin subunit proteins and the assumption that only the highly variant portions of these molecules were exposed (Wolf, 1997). However, the results presented herein suggest that exposed conserved domains of flagellin as well as proteins that interact with these regions could serve as viable antigenic targets to prevent infections caused by ETEC and other important pathogens.

The present invention further investigated the potential of EtpA as a vaccine candidate in the treatment of human enterotoxigenic *Escherichia coli* infections using an animal model. This animal model of enterotoxigenic *Escherichia coli* infection is relevant to investigation of the pathogenesis of human enterotoxigenic *Escherichia coli* infections for several reasons. First, the development of a protective immune response following repeated exposures to enterotoxigenic *Escherichia coli* in these mice parallels previous epidemiologic observations made in children in developing countries suggesting that prior exposures to enterotoxigenic *E. coli* provide protection against subsequent episodes of enterotoxigenic *Escherichia coli* infection and symptomatic diarrheal illness (Steinsland et al., 2003). Similarly, these mouse studies are reminiscent of the results of earlier human volunteer studies demonstrating that prior infection offers protection from diarrheal illness on subsequent challenge (Levine et al., 1979). Second, these are the first experiments to demonstrate that a protein other than the known toxins (Allen et al., 2006) or colonization factor (CFs) might contribute to intestinal colonization, a critical step in the virulence of these pathogens. Likewise, these are the first studies to suggest that a virulence factor other than the intensively investigated CF molecules or toxins might serve as viable targets in vaccine development.

The results discussed herein suggest that the mouse model of colonization may be useful in evaluation of potential enterotoxigenic *Escherichia coli* vaccine candidates, such as EtpA. In its present form the murine model has as its major limitation the fact that mice do not get diarrhea even following prolonged exposures to high doses of enterotoxigenic *Escherichia coli* that would normally cause diarrheal illness in humans. However, the ability to colonize the intestinal mucosa is thought to be a critical parameter in the development of diarrhea, and in vitro studies demonstrate that intimate association of the bacteria with target epithelial cells is required for effective toxin delivery (Dorsey et al., 2006).

Although EtpA appears to facilitate colonization of mouse intestine, the mechanism by which this happens is not completely clear. It is suggested that this protein is largely secreted from the organism and it has been difficult to find EtpA associated with the outer membrane of enterotoxigenic *Escherichia coli*. Indeed EtpA lacks carboxy terminal cysteine residues that have been shown to be important in anchoring other known TpsA adhesins to the bacterial surface (Buscher et al., 2006). However, TcpF a soluble virulence factor of *Vibrio cholerae*, has also been shown to enhance colonization in an in vivo mouse colonization model (Kim and Taylor, 2005). Regardless of the mechanism by which EtpA acts to facilitate colonization, these studies suggest that EtpA contributes to the virulence of enterotoxigenic *Escherichia coli*, and that it may serve as a suitable target in vaccine development.

In the present invention, EtpA was administered via an intranasal route similar to prior studies of the effect of subunit vaccines on intestinal colonization of Campylobacter jejuni in mice (Lee et al., 1999). Despite this, a direct delivery of EtpA and other antigens to the intestinal mucosa may be required to provide optimal protection (Holmgreen and Czerkinsky, 2005; Brandtzaeg, 2006; Walker et al., 2006). Additionally, significant increases in fecal immunoglobulin were not detected following intranasal immunization. This possibly reflects compartmentalization of secretory IgA responses. However, the ability to achieve some degree of protection following intranasal administration may reflect small amounts of antibody that leak from the lamina propria to the mucosal surface (WHO, 2006; Brandtzaeg, 2006). Administration of live, attenuated, orally-delivered vaccines that express multiple relevant antigens will likely afford optimal protection against these important enteric pathogens. However, future enterotoxigenic *Escherichia coli* vaccine strategies will need to take into account the precedent set by highly effective parenterally administered vaccines for other enteric pathogens such as the Vi-EPA conjugate vaccine for *S. typhi* (Lin et al., 2001).

It is important to note that not all enterotoxigenic *Escherichia coli* strains express EtpA. However, previous studies do suggest that EtpA may be among the more highly conserved antigens described to date, being present in ETEC strains of multiple CF groups from diverse geographic origins (Fleckenstein et al., 2006). Further studies will be required to define the true prevalence of strains expressing this molecule. However, the results presented herein point to the promise of novel virulence molecules that might be incorporated into a multivalent broadly protective vaccine.

Additionally, while EtpA appears to contribute to virulence in the murine model, it is not clear how it might contribute to virulence of H10407 and other EtpA-expressing strains in humans. H10407 (CFAI, LT⁺, ST⁺), originally isolated from a Bangladeshi child with severe cholera-like diarrheal illness (Evans amd Evans, 1973), appears to be significantly more virulent than strain B7A (CS6, LT⁺, ST⁺), which is EtpA-negative. In human clinical challenge studies of these two organisms the volume of diarrhea in volunteers that ingested H10407 was nearly two-fold that of those who were infected with the same dose of B7A (Coster et al., 2007).

Taken together, the present invention demonstrates that the interaction of EtpA and flagellin protein of enterotoxigenic *Escherichia coli* play a significant role in bacterial adhesion. More importantly, the present invention demonstrates that EtpA and flagellin protein are useful immunogens that can be targeted to either prevent or treat an enterotoxigenic *Escherichia coli* infection or any infection caused other similar flagellated human pathogens. Furthermore, results presented herein suggest that the murine intestinal colonization model using human enterotoxigenic *Escherichia coli* strains can serve as a platform to examine the contribution of novel candidate virulence molecules such as EtpA to the pathogenesis of these organisms. More importantly, this model may provide a relatively high-throughput, inexpensive avenue for preclinical testing of the viability of newly defined enterotoxigenic *Escherichia coli* antigens in vaccine development.

The present invention is directed to an immunogenic composition, comprising a two-partner secretion protein(s), a flagellin protein or fragments thereof, a pharmaceutically acceptable adjuvant or a combination thereof. The examples of two-partner secretion proteins include but are not limited to the ETEC proteins such as EtpA, EtpB; PA4541 (*Pseudomonas aeruginosa*) or BpaA (*Burkholderia pseudomallei*). Examples of flagellin protein include but are not limited to the full-length flagellin or flagellin subunit derivatives containing highly conserved regions of flagellin molecules similar to the highly conserved regions of *E. coli* flagellin serotype H48, where the highly conserved regions of flagellins include but are not limited to amino acids 1-173 or 400-498. Since the amino acid conservation in these regions is 100%, the conserved regions of flagellin molecules for other gram negative organisms will be similar to that found in *E. coli* flagellin serotype H48. More specifically, the full-length flagellin or the flagellin subunit may be derived from *E. coli* serotype H48. In general, the two-partner secretion protein(s), the flagellin protein or fragments thereof may be a recombinant protein, a peptide, or fusion proteins expressed from a vector. Such a vector may a bacterial vector, a viral vector or a plasmid. Since constructing vectors for therapy is routine in the art, it is contemplated that one of skill in the art can construct any vector expressing the above-mentioned protein(s) based on the disclosure of the present invention. The recombinant protein may be produced in *E. coli* or attenuated bacterial pathogens. Additionally, the recombinant protein, the peptide, or the fusion protein may comprise modified or unmodified amino acids.

The present invention is also directed to a method of preventing an infection caused by flagellated Gram-negative bacteria in an individual. Such a method comprises administering an immunologically effective amount of the immunogenic composition described supra to the individual. Such an administration may induce an antibody response, prevent colonization of the flagellated Gram-negative bacteria in the individual or a combination thereof. Examples of such flagellated Gram-negative bacteria may include but are not limited to enterotoxigenic *Escherichia coli* (ETEC), uropathogenic *E. coli, Salmonella, Pseudomonas aeruginosa, Burkholderia* or other flagellated Gram-negative pathogens. The individual who may benefit from such a method may include but are not limited to a healthy individual, one who is at high risk of developing infection caused by the flagellated Gram-negative bacteria or has been exposed to the flagellated Gram-negative bacteria. Additionally, the immunogenic composition may be administered subcutaneously, intramuscularly, intranasally or mucosally.

The present invention is also directed to an antibody directed against one or more of two-partner secretion protein(s), a flagellin protein or fragments thereof. Such an antibody may be a monoclonal antibody or a chimeric antibody. Additionally, such an antibody may be generated using one or more of the two-partner secretion protein(s), the flagellin or the fragments thereof. The two-partner secretion protein, the flagellin or the fragments thereof used to generate such an antibody may be a recombinant protein, a peptide, a fusion protein or expressed using a vector. The vector may be a bacterial vector, a viral vector or a plasmid that are routinely used in the art. The recombinant protein used to generate such an antibody may be produced in *Escherichia coli* or an attenuated bacterial pathogen.

Furthermore, the recombinant protein, the peptide or the fusion protein may comprise modified or unmodified amino acids. Representative examples of the two partner secretion protein may include but are not limited to EtpA, EtpB, PA4541 or BpaA and those of the flagellin protein may include but are not limited to the full-length flagellin molecules or flagellin subunit derivatives containing highly conserved regions of flagellin molecules similar to the highly conserved regions of *E. coli* serotype H48, where the highly conserved regions of flagellins include amino acids 1-173, or 400-498 (the non-serotype dependent regions of the molecule). Since the amino acid conservation in these regions is 100%, the conserved regions of flagellin molecules for other gram negative organisms will be similar to that found in *E. coli* flagellin serotype H48. More specifically, the full-length flagellin or the flagellin subunit may be derived from *E. coli* serotype H48.

The present invention is further directed to a method of treating an infection caused by a flagellated Gram-negative bacteria in an individual, comprising: administering immunologically effective amounts of the antibody discussed supra to the individual, thereby treating the infection caused by the flagellated Gram-negative bacteria in the individual. This method may further comprise administering a pharmacologically effective amount of an antibiotic toxic to the flagellated Gram-negative bacteria. Such an antibiotic may be administered concurrent with, subsequent to or sequential to the administration of the antibody. Further, the individual who benefits from this method may include but is not limited to a healthy individual, one who is at high risk of developing infection caused by the flagellated Gram-negative bacteria or one who has developed an infection caused by Gram-negative bacteria. The antibody may be administered, inter alia, subcutaneously, intramuscularly, intranasally or mucosally. Examples of the flagellated Gram negative bacteria may include but are not limited to enterotoxigenic *Escherichia coli* (ETEC), uropathogenic *E. coli, Salmonella, Pseudomonas aeruginosa, Burkholderia* or other flagellated Gram-negative pathogen.

The present invention is also directed to a method of preventing diarrhea caused by enterotoxigenic *Escherichia coli* in an individual, comprising: administering an immunogenic composition comprising EtpA or a full-length flagellin or flagellin subunit derivatives containing the highly conserved regions of flagellin molecules such as those found in *E. coli* flagellin serotype H48, wherein the highly conserved regions of flagellins are amino acids 1-173 or 400-498 to an individual. The administration of such an immunogenic composition may induce an antibody response, which prevents colonization of the flagellated Gram-negative bacteria or a combination thereof in the individual. The individual who benefits from this method may include but is not limited to a healthy individual, one who is at high risk of developing infection caused by the flagellated Gram-negative bacteria or one who has been exposed to the flagellated Gram-negative bacteria. Such an immunogenic composition may be administered subcutaneously, intramuscularly, intranasally or mucosally.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, "active immunization" is defined as the administration of a vaccine to stimulate the host immune system to develop immunity against a specific pathogen or toxin.

As used herein, "passive immunization" is defined as the administration of antibodies to a host to provide immunity against a specific pathogen or toxin.

As used herein, "adjuvant" is defined as a substance which when included in a vaccine formulation non-specifically enhances the immune response to an antigen.

Treatment methods will involve preventing an infection in an individual with an immunologically effective amount of a composition containing a secreted two-partner secretion protein(s), a flagellin protein or fragments thereof, a pharmaceutically acceptable carrier or a combination thereof or an antibody generated using the immunogenic composition. An immunologically effective amount is described, generally, as that amount sufficient to detectably and repeatedly induce an immune response so as to ameliorate, reduce, minimize or limit the extent of a disease or its symptoms. More specifically, it is envisioned that the treatment with the immunogenic composition enhances antibody response, prevents colonization of the flagellated Gram-negative bacteria or a combination thereof to prevent the infection caused by the flagellated Gram-negative bacteria.

The immunogenic composition disclosed herein and the antibody generated thereof may be administered either alone or in combination with another drug, a compound, or an antibiotic. Such a drug, compound or antibiotic may be administered concurrently, subsequently or sequentially with the immunogenic composition or antibody disclosed herein. The effect of co-administration with the immunogenic composition or antibody is to lower the dosage of the drug, the compound or the antibiotic normally required that is known to have at least a minimal pharmacological or therapeutic effect against the disease that is being treated. Concomitantly, toxicity of the drug, the compound or the antibiotic to normal cells, tissues and organs is reduced without reducing, ameliorating, eliminating or otherwise interfering with any cytotoxic, cytostatic, apoptotic or other killing or inhibitory therapeutic effect of the drug, compound or antibiotic.

The composition described herein and the drug, compound, or antibiotic may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The immunogenic composition or antibody described herein and the drug, compound or antibiotic may be administered independently one or more times to achieve, maintain or improve upon a therapeutic effect. It is well within the skill of an artisan to determine dosage or whether a suitable dosage of either or both of the immunogenic composition or antibody and the drug, compound or antibiotic comprises a single administered dose or multiple administered doses.

As is well known in the art, a specific dose level of such an immunogenic composition or antibody generated thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

Administration of the immunogenic composition of the present invention and the antibody generated thereof to a patient or subject will follow general protocols for the administration of therapies used in treatment of bacterial infections taking into account the toxicity, if any, of the components in the immunogenic composition, the antibody and/or, in embodiments of combination therapy, the toxicity of the antibiotic. It is expected that the treatment cycles would be repeated as necessary. It also is contemplated that various standard therapies, as well as surgical intervention, may be applied in combination with the described therapy.

As is known to one of skill in the art the immunogenic composition described herein may be administered along with any of the known pharmacologically acceptable carriers. Additionally the immunogenic composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Bacterial Strains and Plasmids

A description of the bacterial strains and recombinant plasmids used in these experiments is given in Table 1.

TABLE 1

Bacterial strains and plasmids

| Strain or Plasmid | relevant genotype or description | reference(s) |
|---|---|---|
| Strain | | |
| H10407 | ETEC serotype O78:H11; CFAI LT$^+$/ST$^+$, EtpA$^+$ | Fleckenstein et al., 2006; Evans and Evans, 1973 |
| Tx-1 | ETEC serotype O78:H12; CFAI, ST$^+$, EtpA$^+$ | Fleckenstein et al., 2006 |
| DS61-1 | ETEC serotype O6:H16; CFAII, LT/ST, EtpA$^+$ | Fleckenstein et al., 2006 |
| DS220-4 | ETEC serotype O11:H33, CFAII, EtpA$^-$ | Fleckenstein et al., 2006 |
| E. coli Top10 | F- mcrA φ(mrr-hsdRMS-mcrBC) φ80lacZφM15 φlacX74 recA1 araD139 φ(araleu) 7697 galU galK rpsL (StrR) endA1 nupG | Invitrogen |
| E. coli LMG194 | F- ΔlacX74 galE thi rpsL ΔphoA (Pvu II) Δara714 leu::Tn10 (TetR) | Invitrogen |
| jf1289 | isogenic etpA mutant | Fleckenstein et al., 2006 |
| jf1412 | fliC mutant; non-motile; Km$^R$ | |
| jf721 | fliD::NKBOR, Km$^R$; non-motile | Dorsey et al., 2006 |
| MG1655 | descendent of prototype E. coli K-12 strain, OR:H48:K- | Jacob-Dubuisson et al., 2001 |
| jf1668 | etpA mutant containing selectable Cm$^R$ cassette generated by introduction of 8590 bp XhoI/HindIII pJMF1019 fragment. etpA deletion verified by PCR primers[primers jf092605.3/jf122205.1] to distinguish etpA::Cm$^R$ (3044 bp) from wild type etpA (1692 bp). | |
| jf876 | ΔlacZYA derivative of H10407, Km$^R$ | Dorsey et al., 2006 |
| jf945 | ΔlacZYA derivative of H10407 | Dorsey et al., 2006 |
| plasmid | | |
| pJY019 | etpBAC expression plasmid | Fleckenstein et al., 2006 |
| pJL016 | etpBA cloned into pBAD/Myc-His A*, native etpA stop codon | |
| pJL017 | etpBA cloned into pBAD/Myc-His A*, with etpA in-frame with myc and 6His coding regions. | |
| pJL030 | etpC gene cloned into pACYC184, Cm$^R$ | |
| pTrcHis B | expression plasmid for polyhistidine fusions, Amp$^R$ | Invitrogen |
| pBADmycHisA | Arabinose-inducible expression plasmid, Amp$^R$ | |
| pFLAG-CTC | expression plasmid vector Amp$^R$ | Sigma |
| pJY044 | FliC$_{MG1655}$ (serotype H48)/pFLAG-CTC expression plasmid.fliC cloned using primers jf011706.1 and jf011706.2 | |
| pKR001b | full-length FliC (H48) (AA residues M$_1$-G$_{498}$) from MG 1655 as 6His fusion in pTrcHis B | |
| pKR005b | residues S$_{174}$-G$_{498}$ FliC$_{MG1655}$ in pTrcHis B | |
| pKR007b | residues M$_1$-F$_{173}$ FliC$_{MG1655}$ in pTrcHis B | |
| pKR008 | full length H11 flagellin amplified from H10407 using primers jf053006.3 and jf053006.5 and cloned into BgII, SnaBI sites of pBAD/Myc-HisC | |
| pKR009 | residues M$_1$-F$_{173}$ FliC$_{H10407}$ (H11) amplified from H10407 using primers jf053006.3 and jf053006.5 and cloned into BgII, SnaBI sites of pBAD/Myc-HisC | |
| pKR011 | residues N$_{174}$-L$_{385}$ FliC$_{H10407}$ (H11) amplified from H10407 using primers jf053006.6 and jf053006.7 and cloned into BgII, SnaBI sites of pBAD/Myc-HisC | |

TABLE 1-continued

Bacterial strains and plasmids

| Strain or Plasmid | relevant genotype or description | reference(s) |
|---|---|---|
| PFliD-FLAG-CTC | FliD gene from MG 1655, amplified using primers jf011706.3/jf100307.5 and cloned into HindIII/BgIII sites of pFLAG-CTC inframe with FLAG tag. | |
| pGPS4 | Tn7-based linker-scanning mutagenesis donor, $Cm^R$ | NEB |
| pGPS5 | Tn7-based linker-scanning mutagenesis donor, $Km^R$ | NEB |

*vector PmeI site was subsequently removed using site-directed mutagenesis (QuikChangeII, Stratagene) with primers jf071706.1 and jf071706.2.

Example 2

Adherence Assays

Bacteria grown overnight in Luria broth from stocks maintained at −80° C. were diluted (1:100) into fresh media and incubated at 37° C., 225 rpm to mid-logarithmic growth phase. Bacteria were then added to target epithelial cells at a multiplicity of infection (MOI) of approximately 10:1. After 1 hour incubation at 37° C., 5% $CO_2$, nonadherent bacteria were removed by repeated washing with RPMI, and cell-associated organisms were recovered by lysis of the epithelial cells in 0.1% Triton-X-100 as described (Fleckenstein et al., 2006).

Example 3

Construction of fliC Isogenic Deletion Mutant

To construct a deletion in fliC, a Kanamycin cassette was amplified from pKD4 using primers jf121905. 1(5'-GGAAACCCAATACGTAATCAACGACTTGCAATATAG GATAACGAATCGTGTAGGCT GGAGCTGCTTC-3'; SEQ ID NO: 1) and jf121905.2 (5'-TGCCAACACGGAGTTACCGGCCTGCTGGATGATCTG CGCTTTCGACATATGATATC CTCCTTA-3'; SEQ ID NO: 2), where underlined sequences represent upstream and downstream regions flanking fliC, respectively in the E. coli K-12 (MG1655) sequence (Blattner et al., 1997). This amplicon was then introduced into H10407(pKD46) as described (Fleckenstein et al., 2006; Datsenko and Wanner, 2000) to replace the fliC gene. Kanamycin-resistant colonies were then screened for motility on soft agar (1% tryptone, 0.7% NaCl, 0.35%. agar).

To complement the resulting strain, jf1412, a flagellin expression plasmid encoding fliC from MG1655 (serotype H48) was constructed. Briefly primers jf011706.1 (5'-AATAATAAGCTTATTGGCACAAGTCATTAATACC-3'; SEQ ID NO: 3) and jf011706.2 (5-AATAAT AGATCTTTAACCCTGCAGCAGAGA-3'; SEQ ID NO: 4) were used to amplify $fliC_{H48}$ from MG1655 genomic DNA (underlined regions of primers represent HindIII and BglII sites, and bold residues indicate fliC start and stop codons, respectively). The resulting amplicon was cloned into pFLAG-CTC yielding pJY044.

Example 4

Linker Scanning Mutagenesis of etpA

To construct a system that would enable efficient screening of etpA mutants, both the etpB and etpA genes were amplified using primers jf031505.1 (5'-AATAATCTCGAGaATG-GTGGTGAAATTCATG-3'; SEQ ID NO: 5) and jf110705.2 (5'-AATAATAAGCTTTTGCCAGTACACCTCACT-3'; SEQ ID NO: 6). The resulting amplicon was digested with XhoI and HindIII and cloned into the corresponding sites of pBAD/Myc-His A placing etpA in-frame with the myc epitope and polyhistidine-encoding regions of the vector. Sit-edirected mutagenesis (QuikChange II, Stratagene) using primers jf071706.1 (5'-CATCATCATCATTGAGT-TCAAACGGTCTCCAGCTTGG-3'; SEQ ID NO: 7) and jf071706.2 (5'-CCAAGCTGGAGACCGTTTGAACT-CAATGATGATGATG-3'; SEQ ID NO: 8) was performed to remove a PmeI site of the vector. The resulting plasmid pJL017, was then used as the target for in vitro transposase (TnsABC)-mediated Tn7-based transprimer linker scanning mutagenesis (LSM) using either pGPS4 or pGPS5 (New England Biolabs) as the transprimer donors. Recombinant plasmids generated by LSM were then digested with XhoI/HindIII to identify insertions within etpA, followed by sequencing using transprimer-specific primers N (5'-ACTT-TATTGTCATAGTTTAGATCTATTTTG-3'; SEQ ID NO: 9) and S (5'-ATAATCCTTAAAAACTCCATTTCCACCCCT-3'; SEQ ID NO: 10) to identify the precise location of the mutation within etpA.

Plasmids containing mapped, non-redundant insertions were then digested with PmeI and religated to remove the majority of the transprimer sequence yielding etpA mutants with 15 bp scar sequences each containing a unique PmeI site. These plasmids were then introduced into E. coli Top10 along with pJL030 containing the etpC gene (required to promote optimal secretion of EtpA) cloned on a compatible vector plasmid (pACYC184). Following induction with arabinose (0.0002%) the resulting AmpR/CmR colonies screened for EtpA secretion by immunoblotting TCA-precipitated supernatants. Plasmids encoding EtpA mutants that were effectively secreted were then introduced into the isogenic etpA mutant jf1668. After confirming EtpA secretion by immuno-blotting these constructs were employed in subsequent adherence and protein interaction studies.

Example 5

Construction of an Isogenic etpA Mutant for Use in Intestinal Competition experiments To create a strain with a selectable marker for competition assays, plasmid pJMF1019 resulting from linker scanning mutagenesis of pJL017 with GPS4 was first used. This plasmid contains a transposon insertion encoding a chloramphenicol resistance ($Cm^R$) cassette at etpA nucleotide position 328. A 8590 bp XhoI/HindIII restriction fragment from pJMF1019 containing this mutagenized etpA locus was then introduced into H10407 by lambda redmediated allelic exchange as previously described (Wolf, 1997) to generate the etpA-negative, Cm$^R$ mutant (jf1668) used for the competition experiments. Verification of the etpA deletion was performed by PCR using primers jf092605.3 (5'-CAGATTGTGGCAGGTTCA-3'; SEQ ID NO: 11) and jf122205.1 (5'-CTAAAACAGAATCCCGCTATC-3'; SEQ ID NO: 12) to distinguish the mutant etpA::Cm$^R$ sequence (3064 bp) from the wild type etpA sequence (1692 bp). Competent jf1668 cells were then used as the recipients for complementing plasmids derived from pJL017 as outlined above.

Following induction with 0.0002% arabinose, production of rEtpA (or mutant versions of this protein) was confirmed by immunoblotting TCA-precipitated culture supernatants (Fleckenstein et al., 2006).

Example 6

Interaction of EtpA with Host Cell Surface Proteins

To examine potential binding of EtpA to intestinal epithelial cells, E. coli Top10(pJY019) were grown overnight, diluted in 1:100 in 200 ml of fresh Luria broth containing ampicillin (100 .mu.g/ml), grown for an additional three hours, then induced with arabinose (0.0002%) for 2 hours. E. coli Top10(pBAD/mycHisA) was grown in an identical fashion. Supernatants were sterile filtered, and concentrated (200.times.) through a 100 kDa MWCO filter, and dialyzed overnight against PBS, pH 7.2. Concentrated proteins were added to HCT-8 cells grown on glass coverslips at a final concentration of 12.5 .mu.g/ml in PBS. After incubation with the cells at 4.degree. C. for one hour, cells were washed, and fixed with ice-cold methanol. Bound EtpA was detected by immunofluorescence using rabbit polyclonal anti-EtpA primary antibodies (1:250; Dorsey et al., 2006), and secondary goat anti-rabbit IgG conjugated to Alexa Fluor 594 (Molecular Probes) (1:500). During subsequent washes with PBS, 4',6-diamidino-2-phenylindole, dihydrochloride (DAPI) was added at a final concentration of 300 nM. Immunofluorescence images were acquired on a Zeiss Axioplan microscope, saved as ZVI (Zeiss) files. Pseudocolor images were then created in ImageJ (v1.36b) (rsb.info.nih.gov/ij/) without adjustment to contrast or brightness of the original images by merging red and blue channel data.

Purified recombinant EtpA was biotinylated by incubation with 2 mM biotin LC hydrazide (Pierce) for 4 hours at 4° C. Labeled protein was then dialyzed overnight in PBS at 4° C. to remove excess biotin. Target epithelial cell monolayers were fixed with 3% paraformaldehyde, then washed with PBS, and blocked with a solution of 1% BSA in PBS for 1 hour. Binding of EtpA was first investigated by adding biotinylated protein at final concentrations of 0.05, 0.1, and 0.2 µM, and incubating at 37° C. for 1 hour. After washing with PBS, bound label was detected by using streptavidin-HRP (1:10000) and tetramethylbenzidine/$H_2O_2$ (TMB) peroxidase substrate (Kierkegaard & Perry Laboratories). Reactions were stopped after significant color development by the addition of 1M H2SO4, and the $OD_{405}$ was determined spectrophotometrically. Similar experiments were then conducted using labeled EtpA at a final concentration of 0.05 µM combined with increasing amounts of unlabeled EtpA.

Example 7

Expression and Purification of Recombinant EtpA

LMG194(pJY019) (Fleckenstein et al., 2006) or E. coli Top10(pJY019) expressing the EtpBAC two-partner secretion system was grown overnight in Luria broth containing ampicillin (100 µg/ml) at 37°, 225 rpm. Overnight cultures were diluted 1:100 in 400 ml of fresh media, grown to $OD_{600}$ of ≈0.5, and induced by the addition of arabinose (0.0001 mM final concentration) for 4 hours. Supernatant was sterile-filtered through a 0.22 µm filter (GP Express plus, Millipore), then concentrated (≈150×) via filtration through a 30,000 MWCO filter (YM30, Millipore). The retentate was desalted using buffer exchange with 50 mM sodium phosphate, 150 mM NaCl, pH 7.2 and concentrated further to a final volume of ≈1 ml (≈400×) following centrifugation in a 100,000 MWCO filter (YM-100 Centriplus, Millipore), then loaded onto a Sephacryl S-300 high resolution gel filtration column. Elution of protein (flow rate of 0.5 ml/minute) was monitored by absorbance at 280 nm and the profile recorded using LP Data View software (BioRad). 1 ml fractions were then collected (BioFrac, BioRad) and stored at 4° C. prior to analysis by SDS-PAGE and immunoblotting.

Alternatively, recombinant polyhistidine-tagged EtpA was expressed from E. coli Top10 containing both the etpBA expression plasmid, pJL017 and the etpC expression plasmid pJL030. pJL017 contains both etpB and etpA genes cloned in-frame with myc and polyhistidine tags on pBAD/Myc-His A. pJL030 contains the etpC gene cloned on pACYC184. Following induction of Top10(pJL017/pJL030) with arabinose, supernatant was concentrated as above and tagged EtpA molecules were recovered in highly-purified form by metal affinity chromatography.

Example 8

Immunoblotting and Antibodies

To detect EtpA, immunoblotting was performed using highly cross-absorbed anti-EtpA (Fleckenstein et al., 2006) rabbit polyclonal rabbit antisera at a dilution of 1:2000, and goat anti-rabbit immunoglobulin G(Fc)-horseradish peroxidase (1:60,000; Pierce). Rabbit polyclonal antisera raised against E. coli (MG1655) flagella (Majander et al., 2005) were used to detect flagellin molecules. Affinity purification of these antibodies was performed by absorption against recombinant full-length flagellin (H48, MG1655) immobilized on nitrocellulose followed by elution of FliC-specific antibody in 100 mM glycine, pH 2.5 and subsequent neutralization with 1M Tris, pH 8.0 as previously described (Harlow et al., 1999). Additional rabbit polyclonal anti-flagellin specific antisera were subsequently generated against the recombinant full-length polyhistidine-tagged (H48) flagellin as well as the peptide encompassing the $1^{st}$ 173 amino acids of this molecule, followed by affinity purification as outlined above.

All blocking and incubation steps were performed at room temperature in Tris-buffered saline (pH 7.4) containing 0.05% Tween 20 and 5% milk. Detection was carried out with a luminal-based chemiluminescent substrate (SuperSignal; Pierce). To examine relative amounts of EtpA produced by ETEC strains, 1.2 ml of overnight cultures in Luria broth was spun at 5,000 rpm for 3 minutes. 1 ml of culture supernatant was then concentrated to a final volume of 50 .mu.l using (10 kDa MWCO) centrifugal concentration devices (Millipore), after which 20 .mu.l was analyzed by immunoblotting as above. ImageJ (v1.36, Max OS X, rsb.info.nih.gov/ij/) was used in subsequent densitometry measurements of scanned immunoblots films.

Example 9

Identification by Mass Spectrometry

The protein bands of interest were excised from Coomassie-stained polyacrylamide, destained, and placed in 25 mM ammonium bicarbonate and allowed to expand. Following digestion of the excised band with sequencing-grade trypsin (Promega, Madison, Wis.) for 16 hours at 37° C., the resulting peptides were extracted, and the sample was subjected to analysis by mass spectrometry. MALDI-ToF mass spectra were recorded on a Bruker Ultraflex MALDI-TOF/TOF reflecting time-of-flight mass spectrometer (Bruker Daltonics, Bremen, Germany). Matrix-related ions and trypsin autolysis products were used for internal spectra calibration. Locally installed PROWL for Intranet software (Proteometrics) was used to search a current non-redundant database downloaded from NCBI.

Example 10

Cloning, Expression and Purification of Recombinant Flagellin Molecules

To clone the full-length fliC (H48) gene, primers jf030106.1 (5'-AATAAT AGATCTATGGCACAAGTCATTAATACC-3'; SEQ ID NO: 13) and jf030106.2 (5'-AATAAT AAGCTTTACCCTGCAGCAGAGACAGAAC-3'; SEQ ID NO: 14) were used to amplify fliC from MG1655 genomic DNA. The product was then digested with BglII and HindIII (underlined) and ligated into the corresponding sites on pTrcHisB (Invitrogen) in-frame with the polyhistidine encoding region to produce pKR001b. Primers jf050206.1 (5'-AATAATAGATCTAGCGTTAAAAATAACGATACA-3'; SEQ ID NO: 15) and jf030106.2 were used to amplify and clone the region encoding amino acids 174-498 [FliC$_{174-498}$] to produce pKR005b. Finally, the region encoding residues 1-173 of FliC was amplified using primers jf030106.1 and jf050206.2 (5'-AATAAT AAGCTTTAAAACCATCAAGGCCAAGAGT-3'; SEQ ID NO: 16) and cloned into pTrcHisB to produce pKR007b. These resulting plasmids, were then introduced into *E. coli* Top10 (Invitrogen), which does not produce detectable amounts of native flagellin (Hayashi et al., 2001), and expression of the corresponding recombinant flagellin molecules was induced with 0.2 mM arabinose. Recombinant flagellin molecules with myc and polyhistidine tags at their carboxy terminal ends were purified from clarified bacterial lysates using nickel-affinity chromatography (HisTrap, Pharmacia).

Example 11

In Vitro Protein-Protein Interaction Studies (a) Membrane-Based Protein Interaction Studies For these studies of protein-protein interaction, varying amounts of target (bait) proteins were dotted and absorbed onto the surface of nitrocellulose filter strips. Prey proteins were biotinylated with 2 mM biotin-LC-hydrazide (Pierce) for 1 hr at 4° C. in a total volume of 0.5 ml of PBS. Unconjugated biotin was removed by overnight dialysis against PBS. After blocking nitrocellulose strips with 3% non-fat dry milk in PBS for 30 min at room temperature, biotinylated prey proteins (10 µg/ml) in PBS were added to the strips and incubated for 1 hour at room temperature. Strips were washed 5 times with PBS to remove traces of unbound prey protein. Bound biotinylated prey proteins were detected with streptavidin-HRP (1:20,000; Sigma) using chemiluminescent substrate (Supersignal, Pierce).

(b) Co-Immunoprecipitation

Anti-EtpA IgG polyclonal antibodies were first purified from highly cross-absorbed anti-EtpA antisera (Fleckenstein et al., 2006) by protein G affinity column chromatography (HiTrap ProteinG, Amersham Biosciences). Preimmune sera from the same rabbit were treated in an identical fashion. The resulting antibodies (200 µg) were then coupled to solid support gel matrix (AminoLink Plus, Seize, Pierce) using a sodium cyanoborohydride (50 mM) in phosphate buffered saline, pH 7.0. After quenching the reaction with 1M TrisHCl, and washing with 1M NaCl, resin containing anti-EtpA antibodies was equilibrated in binding buffer (140 mM NaCl, 8 mM sodium phosphate, 2 mM potassium phosphate, 10 mM KCl, pH 7.4). Concentrated supernatants from ETEC strains were dialyzed against binding buffer, concentrated approximately 5 fold to a final volume of 0.4 ml, then incubated overnight at 4° C. with matrix containing either pre-immune IgG or anti-EtpA (IgG) antibodies. The matrix was then washed 3× with buffer (25 mM Tris, 150 mM NaCl, pH 7.2) Bound proteins were eluted (ImmunoPure, IgG Elution Buffer, pH 2.8, Pierce), separated by SDS-PAGE, and transferred to nitrocellulose for subsequent immunoblotting.

(c) Molecular Pull-Down Assays

Polyhistidine-tagged flagellin molecules prepared by metal affinity chromatography, and EtpA purified by S-300 molecular sieve chromatography, were added together in solution in a molar ratio of 1:1 (approximately 150 pmol each) in PBS, pH 7.4 to a final volume of 3 ml. After incubation for 1 hour at 4° C. polyhistidine tagged proteins and interacting EtpA were pulled down by the addition of 100 µl of Talon (Co$^{2+}$) metal affinity bead suspension in PBS. Beads were then washed three times to remove unbound proteins. After incubation for an additional hour at 4° C., and washing with PBS, bound proteins were released from Talon beads by incubation in SDS-PAGE sample buffer and used for immunoblotting. FLAG pull-down experiments were performed in a similar fashion, using anti-FLAG (M2) affinity gel (Sigma).

Example 12

Protein Sequence Analysis (In Silico)

To identify potential domains within EtpA, the amino sequence from residues 73-1787 was analyzed using algorithms located on the PredictProtein server. Molecules identified by PSI-BLAST (Altschul et al., 1997) as having regions of homology to EtpA were then used in CLUSTALW (Chema et al., 2003) alignments www.ebi.ac.uk/clustalw/. Regions of homology between EtpA and flagellin were then superimposed on 3D structure of flagellin (Yonekura et al., 2003) using Protein Workshop (Moreland et al., 2005) (v1.35 www-.pdb.org/robohelp/viewers/proteinworkshop.htm).

Example 13

Transmission Electron Microscopy

For in situ immunogold labeling of EtpA, a protocol similar to that described by Jin and He, 2001, was used. Briefly, 10 µl suspensions of live bacteria were applied to the surface of UV-sterilized Formvar/carbon-coated nickel grids (FCF300-Ni, Electron Microscopy Sciences, Hatfield, Pa.). Bacteria were grown on the surface of grids in a humidified chamber at 37° C. for approximately 4 hours followed by immediate fixation by 2% formaldehyde/0.5% glutaraldehyde solution in 50 mM sodium cacodylate, pH 7.2. Immunogold detection was then carried out using highly cross-absorbed anti-EtpA polyclonal rabbit antisera (Fleckenstein et al., 2006) (1:50) or affinity purified anti-flagellin antibodies followed by anti-rabbit IgG gold (10 nm) conjugate (Sigma). Negative staining was then carried out in 1% phosphotungstic acid, pH 6.5.

Example 14

Intestinal Colonization

The previously described model of murine intestinal colonization (Allen et al., 2006) was used in the competition experiments between etpA mutant jf1668 complemented with EtpA expression plasmid pJL017, or the same mutant complemented with pJMF1087 which expresses EtpA that has lost the ability to bind to FliC following introduction of a linker mutation.

Briefly, 10 mice were pre-treated with streptomycin for 48 hours prior to challenge to facilitate colonization with ETEC. Approximately 12 hours prior to challenge, mice were fasted and placed on water alone and were then given cimetidine 2 hours before inoculation. Each mouse then received $1 \times 10^4$ cfu of both jf1668 (pJL017) and $1 \times 10^4$ cfu of jf1668 (pJMF1087) together in a final volume of 0.4 ml by gavage. Immediately following the challenge, the water supply for the mice was changed to include ampicillin (50 µg/ml) and arabinose (0.0002%) to maintain plasmid selection and to induce production of rEtpA, respectively. Twenty-four hours after challenge, mice were sacrificed and intestinal lysates were prepared by incubation in saponin. Lysates diluted in PBS were then plated onto Luria agar plates containing 20 µg/ml of chloramphenicol and 100 µg/ml of ampicillin. Following overnight incubation at 37° C., colony PCR was performed using primers jf122205.1 and jf092605.3 to generate ≈1690 bp amplicon that was subsequently digested with PmeI to distinguish the WT amplicon generated from pJL017 from the mutant amplicon containing a PmeI site.

To examine the role of flagella in intestinal colonization with ETEC, 10 mice were challenged simultaneously by gavage with approximately $1 \times 10^4$ cfu of strain jf876 containing a $Km^R$ cassette in the lacZYA locus and an equal number of jf1412 (containing an identical $Km^R$ cassette in the fliC gene) in a final volume of 0.4 ml. After 24 hours, dilutions of intestinal lysates (Allen et al., 2006) were plated onto Luria agar plates containing Km (25 µg/ml) and the β-galactosidase indicator, Xgal (5-Bromo-4Chloro-3-Indolyl-β-D-galactopyranoside) (Maloy et al., 1996) permitting visual identification of the ΔfliC strain (blue) relative to the WT (white). The competitive index (CI) for each colonized mouse was then calculated as follows: CI=[(mutant (blue)/wild type (white))$^{output\ cfu}$/mutant/wild type)$^{input\ CFU}$] where the input fraction was determined directly by colony counting (cfu) prior to preparation of the inoculum.

Example 15

Immunization of Mice with Recombinant Flagellin and Subsequent ETEC Challenge

After obtaining preimmune sera, groups of 10 mice were immunized with either 7.5 µg of IVX908 (Protillin, ID Biomedical), a mucosal adjuvant based on Neisseria outer membrane proteins non-covalently complexed to LPS (10 µg) or with IVX908 (7.5 µg) rFLiC (H48, (30 µg) in a total volume of 20 µl (10 µl/nostril) on days 0, 25, 48 and 66. Mice in both groups were then challenged 2 weeks after the last immunization with $1 \times 10^4$ cfu of j876, the lacZYA::$Km^R$ version of ETEC H10407 (flagellar serotype H11). Twenty-four hours following challenge, mice were sacrificed and intestinal lysates dilute in PBS were plated onto Luria agar plates containing Km (25 µg/ml) to assess colonization. IVX908 was supplied by Dr. James Dale.

Example 16

Assessment of Murine Immune Responses Following Vaccination with Recombinant Flagellin Following the above-mentioned immunization, sera from mice were tested for reactivity to full-length, serotype specific and conserved regions of both $FliC_{H48}$ and $FliC_{H11}$. Briefly, the respective recombinant polyhistidine-tagged proteins were diluted to a final concentration of 4 µg/ml in 0.1M NaHCO$_3$ buffer, pH 8.6. Wells of ELISA plates were coated overnight at 4° C., washed with TBS (Tris buffered saline) containing 0.05% Tween-20 and blocked for 1 h at 37° C., plates were washed with TBS-T (Blocker, Pierce). Dilutions of immune and preimmune mouse sera were prepared in 1% BSA in TBS-T. After incubation for 1 hour at 37° C., plates were washed with TBS-T and secondary goat anti-mouse (IgA, IgM, IgG) secondary antibody were added at a final concentration of 1:10,000. After incubation for 1 hour at 37° C., plates were washed and developed with TMB Peroxidase substrate (3,3',5,5'-Tetramethylbenzidine). Absorbance measurements were determined kinetically at a wavelength of 620 nm.

To measure fecal antibodies, 5 fresh fecal pellets were obtained from each vaccinated and control mouse. These pellets were immediately resuspended in fecal reconstitution buffer containing Tris (10 mM), NaCl (100 mM), Tween-20 (0.05%) and sodium azide (5 mM) at pH 7.4. Samples were vortexed to homogeneity, and spun at 1500×g at 4° C. for 10 minutes to remove insoluble material. Supernatants were saved and stored at −80° C. for subsequent analysis.

Example 17

Statistical Analysis of Results

Comparisons of data were performed using the nonparametric Mann-Whitney test (two-tailed) unless otherwise specified. All calculations were performed using Prism v4.0c, and InStat v3.0 (GraphPad Software).

Example 18

EtpA and Intact Flagella are Required for Effective Adherence to Target Epithelial Cells Previous studies had shown that EtpA protein (Fleckenstein et al., 2006), a homologue of other TPS adhesins (Buscher et al., 2006), promotes adherence of ETEC strain H10407 to epithelial cells. Since the delivery of heat labile toxin by ETEc requires the production of intact flagella (Dorsey et al., 2006) and flagella have been shown to be involved in adherence of other varieties of pathogenic E. coli to host cells (Pratt and Kolter, 1998), the present invention examined the contribution of flagella to enterotoxigenic Escherichia coli adherence. In this regard, it was observed that both EtpA and the production of intact flagella were required for effective adherence to target intestinal epithelial cells in vitro (FIG. 1A). Mutant strains lacking either the production of flagellin (fliC) or the capacity to assemble flagellin monomers into intact flagella (fliD), failed to adhere to epithelial cells.

Figure 1B:
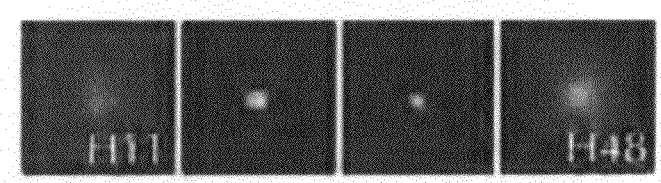
Figure 1B:
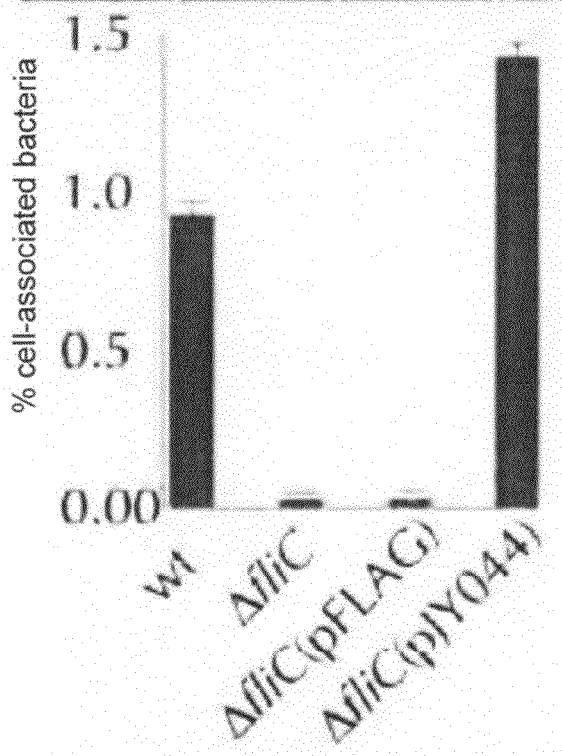
Figure 1C:
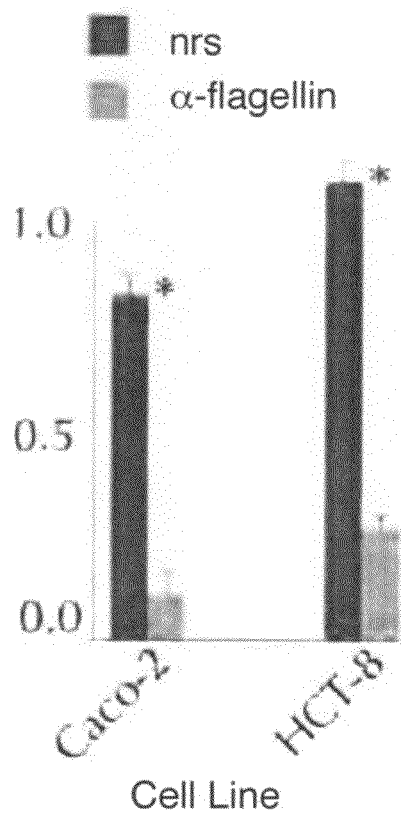

To examine whether the contribution played by flagellin in adherence was dependent on a particular H serotype, an isogenic strain in which the fliC gene coding for H11 flagellin had been deleted, was first complemented with a recombinant plasmid pJY044 expressing the fliC (H48) gene from *E. coli* K-12 (MG1655). Expression of FliC(H48) in this fashion restored both motility and the ability to adhere to host epithelial cells (FIG. 1B). It was also observed that affinity purified anti-flagellin antisera raised against H48 flagella effectively inhibited adherence of ETEC H10407 (H11) to target epithelial cells, suggesting that adherence was independent of serotype-specific domains of flagellin (FIG. 1C).

Figure 1D:
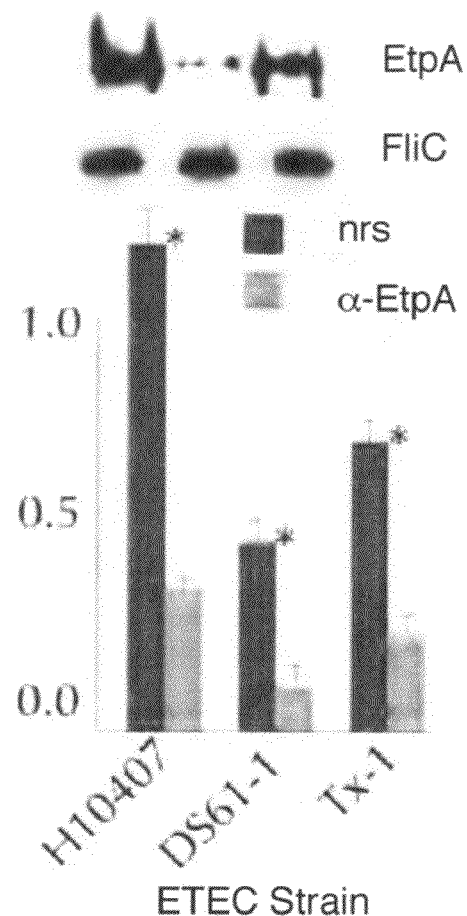

To further demonstrate that EtpA function was not dependent upon a unique *E. coli* background, additional motile EtpA-producing enterotoxigenic *Escherichia coli* strains expressing other flagellin serotypes were examined to determine whether antibodies directed against EtpA would similarly inhibit adherence. Anti-EtpA antibodies inhibited adherence against EtpA-producing enterotoxigenic *Escherichia coli* belonging to each of the serotypes tested (H11, H12, and H16) (FIG. 1D). Additionally, the levels of EtpA expression (inset immunoblot, FIG. 1D) by different enterotoxigenic *Escherichia coli* strains appeared to parallel the adherence phenotype.

Figure 1E:
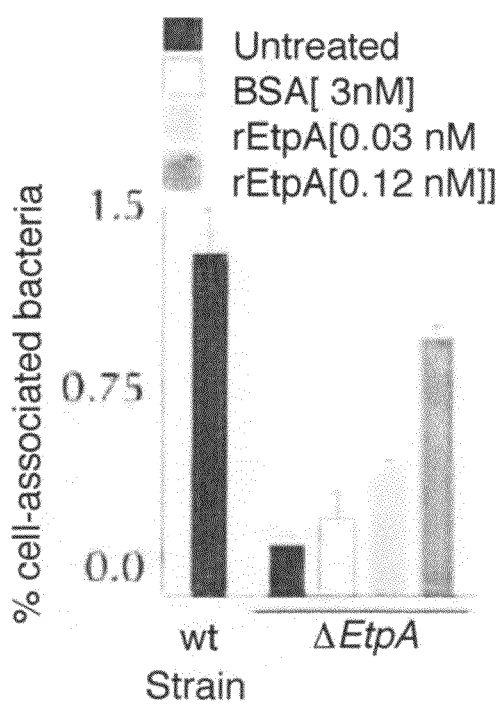

Furthermore, addition of exogenous rEtpA restored the ability of the etpA mutant to adhere in a dose dependent fashion (FIG. 1E). Conversely, addition of rEtpA to H10407-P, which lacks the large plasmid encoding both EtpA and fimbrial CFA/I antigens, failed to complement the adherence defect in this strain, suggesting that EtpA acts in concert with established adhesins.

Example 19

Interaction of EtpA with the Host Cell Surface

One mechanism by which EtpA might promote adherence would be to interact directly with host cells (Lindenthal and Elsinghorst, 2001). Immunofluorescence images of HCT-8 cells obtained following incubation with recombinant EtpA demonstrated significant amounts of EtpA (FIG. 2A) on the cell surface compared to controls (FIG. 2B). Likewise, purified labeled EtpA bound specifically to the surface of these cells (FIG. 2C). Additionally, polyclonal antibodies against EtpA prevented this interaction (Table 2).

TABLE 2

Anti-EtpA antisera inhibits binding of biotinylated rEtpA to target HCT-8 cells.

| Antibody | OD$_{405\,nm}$ | p* |
|---|---|---|
| Preimmune | 0.67 ± 0.07 | ~0.007 |
| α-EtpA | 0.19 ± 0.01 | |
| none | 0.72 ± 0.07 | |

*student's t test (2-tailed, paired samples)

Example 20

EtpA Interacts with Flagellin

It has been demonstrated that EtpA is largely secreted from enterotoxigenic *Escherichia coli*. Theoretically, for EtpA to function as an adhesin, it would not only need to interact with the host cell, but would also need to retain contact with the surface of the bacterium. EtpA was not determined to be associated with the bacterial envelope either by immunofluorescence or in immunoblots of outer membrane preparations from either recombinant strains or the H10407 prototype. However, attempts to purify full-length EtpA glycoprotein from recombinant *E. coli* expressing the etpBAC locus serendipitously alluded to a potential mechanism of action for EtpA.

Figure 3B:
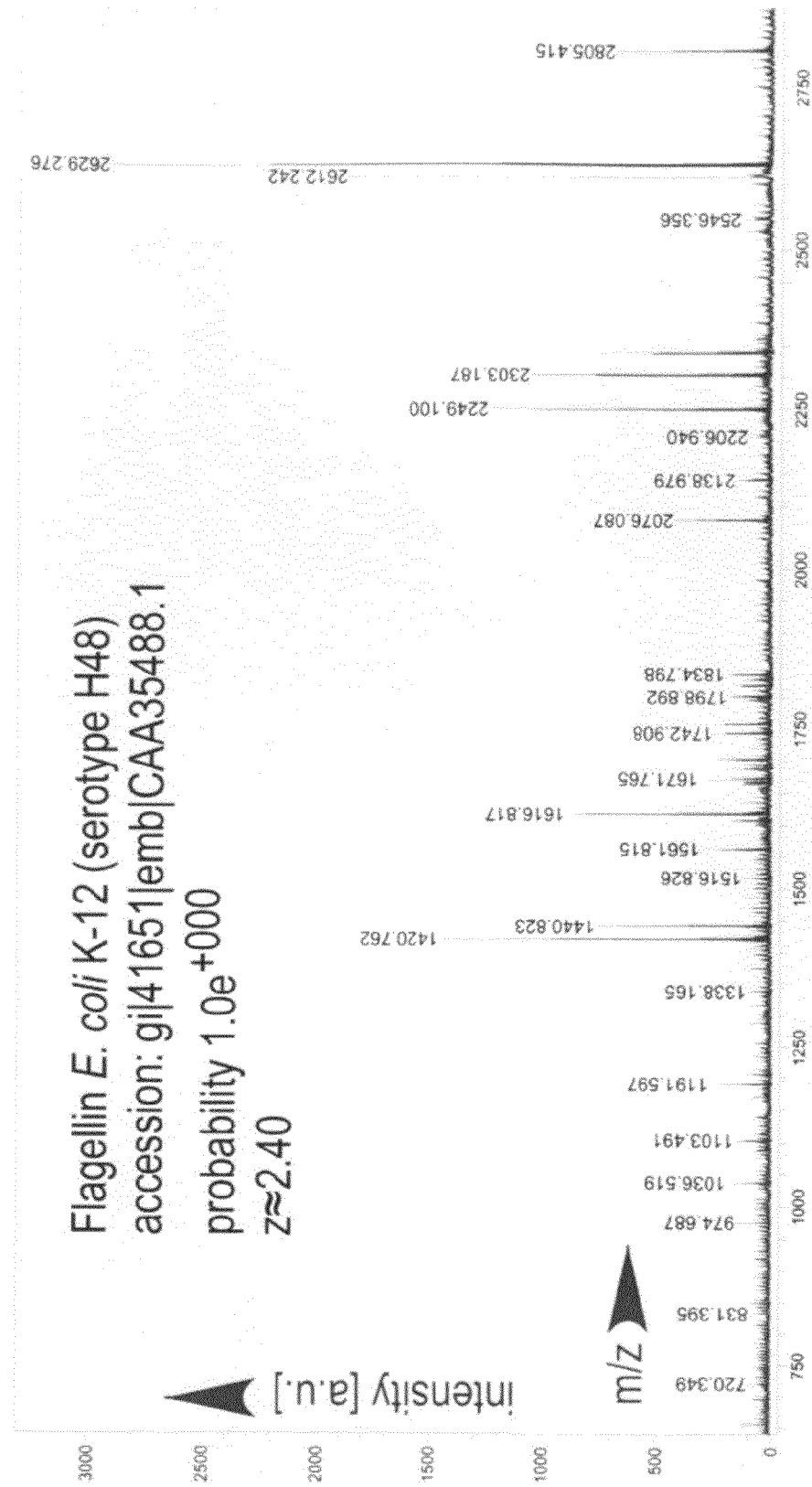

Recovery of recombinant EtpA from culture supernatants of *E. coli* LMG194(pJY019) was complicated by the repeated co-isolation of a second protein of approximately 50 kDa despite concentration of supernatants through filters of high molecular weight retention size (100 kDa) or attempted separation of these molecules by gel filtration column chromatography (FIG. 3A). Since column chromatography can reveal important protein interactions (Golemis and Adams, 2005), the protein co-purified with EtpA was analyzed by MALDI-TOF and definitively identified as flagellin from *E. coli* K-12 (serotype H48), the same serotype as the recombinant strain used in the expression (probability 1.0, Z score=2.40) (FIG. 3B). Similar results were obtained using this purification strategy with culture supernatants from ETEC strain H10407 (serotype O78:H11). All EtpA-containing fractions also contained flagellin as identified by immunoblotting (FIG. 3C), suggesting that EtpA can interact with flagellin molecules from different H serotypes.

Co-immunoprecipitation (co-IP) experiments using anti-EtpA polyclonal antisera (Fleckenstein et al., 2006) and culture supernatants from H10407 suggested that FliC (H11) and EtpA interact (FIG. 3D). Using culture supernatants from strain jf721, which makes FliC, but cannot assemble it into intact flagella due to a mutation in the fliD gene (Dorsey et al., 2006), no difference was observed in the ability of EtpA to interact with flagellin, suggesting that EtpA binds predominately to the monomeric form of this protein.

Since previous studies had shown that glycosylation of EtpA, a process dependent on the etpC gene, modulated adherence of H10407 to intestinal epithelial cells (Fleckenstein et al., 2006), whether post-translational modification of EtpA by glycosylation influenced its interaction with FliC was investigated. However, expression of non-glycosylated EtpA by the etpC mutant did not appear to affect this interaction (FIG. 3D). This is consistent with prior studies demonstrating different effects on adherence in the etpC mutant which were dependent on the target cell line used in vitro, and suggests that glycosylation of EtpA modifies binding of this protein to host receptors.

Additionally, co-immunoprecipitation experiments with culture supernatants from other ETEC strains were performed to demonstrate further that this interaction was specific for EtpA and that it was not dependent on a particular flagellar serotype. Although flagellin from motile EtpA-negative strain DS220-4 (O11:H33) could not be immunoprecipitated, both EtpA and flagellin were identified in immunoprecipitates of EtpA-producing strain TX-1: (O78:H12) (FIG. 3D).

Furthermore, different monomeric flagellin proteins from two different serotypes were immobilized to serve as "bait" for biotin-labeled EtpA or control molecules. Both flagellins (FliC$_{H11}$, and FliC$_{H48}$) captured labeled EtpA, but not the labeled control protein (BSA) (FIG. 3E).

Example 21

EtpA Mimics and Interacts with Conserved Regions of Flagellin

Figure 4A:
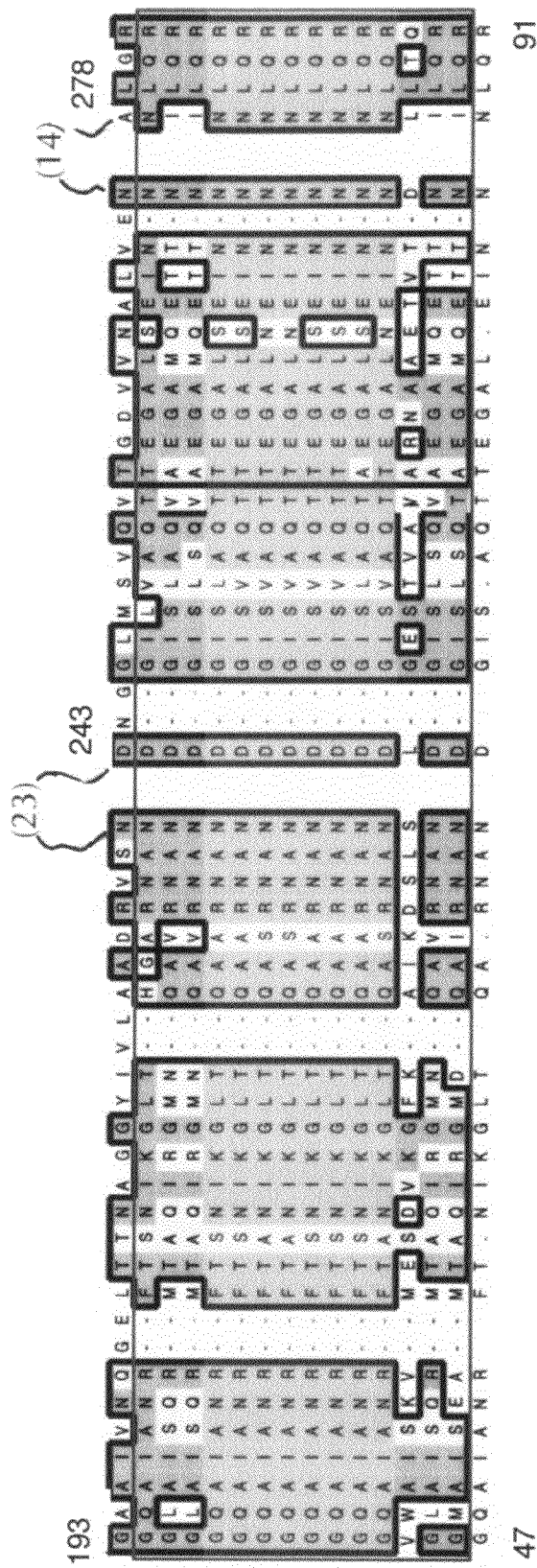

The results discussed supra demonstrate that EtpA was able to interact with monomeric flagellin molecules belonging to multiple flagellar serotypes, and suggested a possible interaction of EtpA with highly conserved regions of these molecules. To define potential functional domains within EtpA, position specific iterative BLAST (PSI-BLAST) searches (Altschul et al., 1997) were performed. As predicted, these searches identified multiple known or potential bacterial adhesins. Interestingly, these searches also identified serial regions of subtle homology with the amino and carboxy terminal regions of multiple flagellin molecules (FIG. 4A-4B), thus, raising the possibility that EtpA interacted with multiple serotypes by mimicking these conserved domains.

To further test this hypothesis, recombinant MG1655-based (H48) polyhistidine-tagged flagellin proteins representing the full-length molecule including the unique serotype-determining region, as well as a truncated version consisting of amino acids 1-173 (the conserved N-terminal domain), and third peptide containing amino acids 174-498 were constructed. The conserved N-terminal domain was both necessary and sufficient to pull down EtpA (FIG. 4C). In addition, affinity-purified polyclonal rabbit anti-sera generated against either the full-length recombinant H48 flagellin or the conserved N-terminal (1-173) region significantly inhibited adherence of ETEC H10407 (O78:H11) to Caco-2 cells (FIG. 4D). These data implicate the participation of highly conserved regions of flagellin molecules in both EtpA binding and in the adherence process.

Example 22

EtpA Binds to Conserved Regions of Flagellin at Flagellar Tips

Figure 5A:
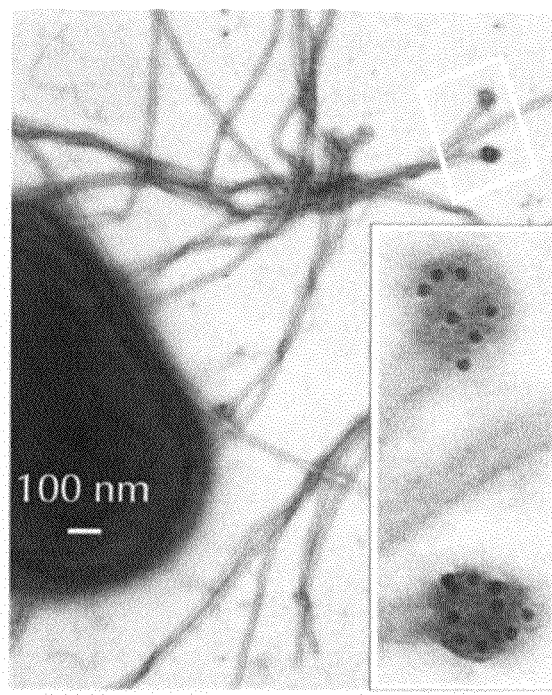
Figure 5B:
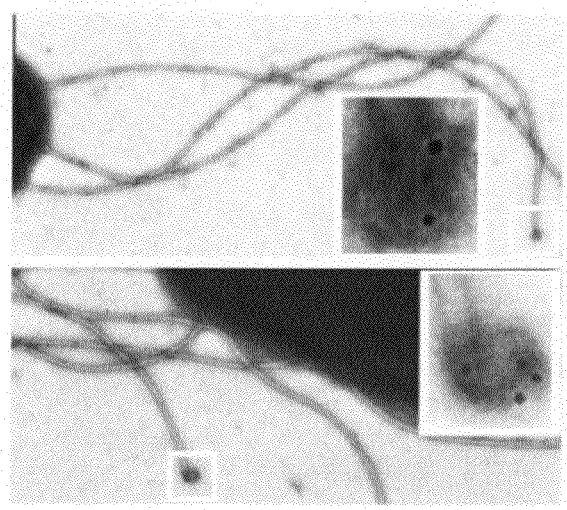
Figure 5C:
Figure 5D:
Figure 5E:
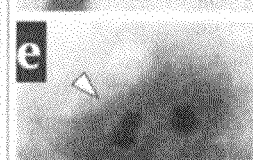
Figure 5F:
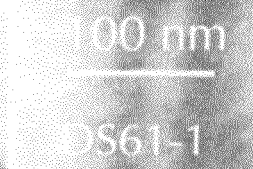
Figure 5I:
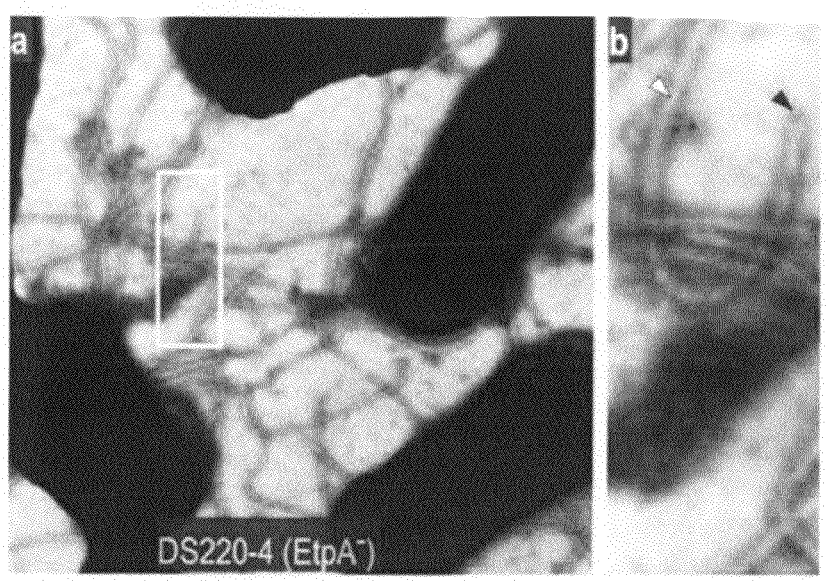
Figure 5I:
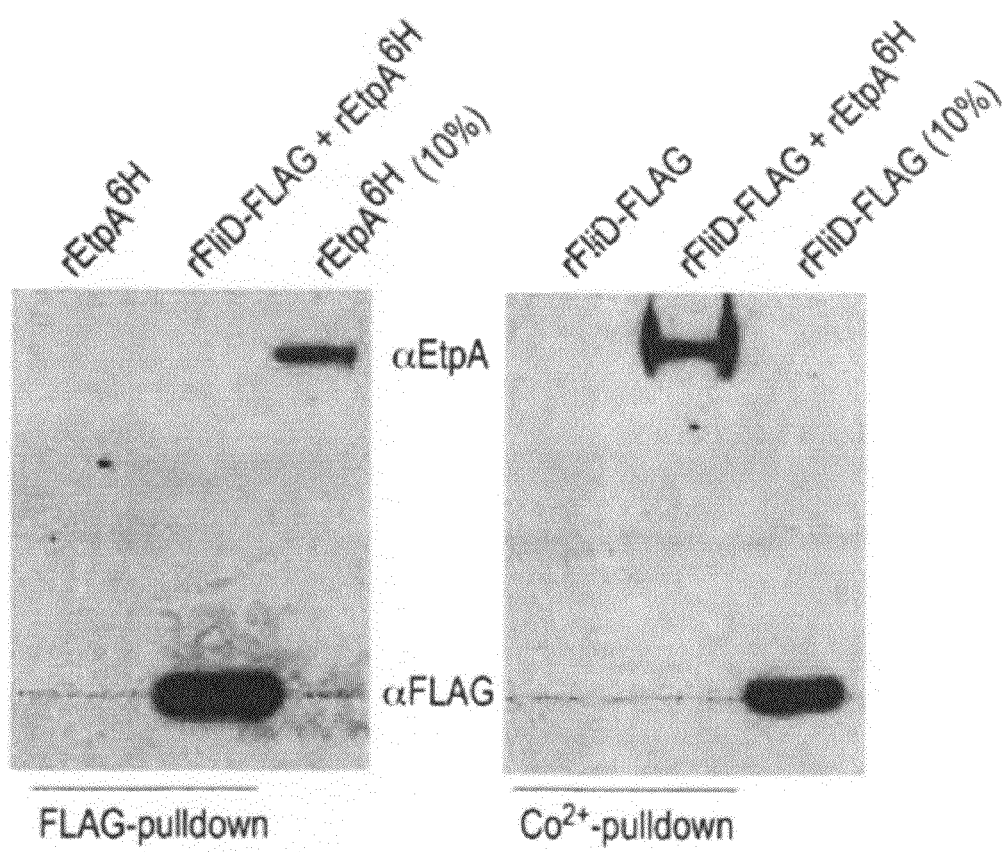

Present models of flagella strongly suggest that upon polymerization, conserved regions of flagellin are largely buried within shaft of these structures (Yonekura et al., 2003). It was however, hypothesized that EtpA could potentially interact with these conserved regions prior to polymerization of the monomers into the shaft at the tips of the flagella. Accordingly, in situ immunogold labeling studies indicated that these conserved regions are available exclusively at the tips of flagella (FIGS. 5A-5C). Likewise, EtpA bound largely at the tips of intact flagella from enterotoxigenic *Escherichia coli* strains belonging to different serotypes with only occasional binding along the flagellar shaft (FIGS. 5D-5F). Conversely, examination of an EtpA negative motile ETEC strain revealed virtually no binding of immunogold conjugate (FIGS. 5G-5H). Because EtpA appeared to be concentrated at the tips of flagella, the possibility that rEtpA might also interact with the flagellar cap protein, FliD was investigated. However, no evidence was found for this in molecular pull-down experiments (FIG. 5I).

Taken together, these studies suggested that EtpA could function as a molecular bridge between conserved regions of the flagellin molecule and the host cell. Preferential binding of EtpA to conserved regions of flagellin could theoretically occur at the tips of growing flagella where these domains would potentially be exposed prior to incorporation of FliC monomers into the flagellar cylinder, or as these molecules leak (Komoriya et al., 1999) from ends of the flagella.

Example 23

Figure 6E:
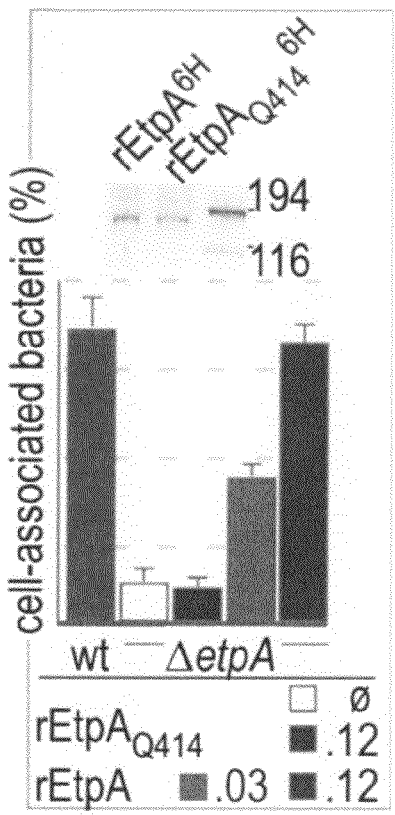

EtpA-Mediated Adherence and Intestinal Colonization Require Interaction with Flagellin To investigate whether the EtpA-flagellin interaction was required for the adherence phenotype, linker scanning mutagenesis (Goff and Prasad, 1991) of etpA was performed, which resulted in the generation of EtpA molecules altered by insertion of either a stop codon or an in-frame scar (5-amino acids) (FIG. 6A). In general, mutations within the repeat region of etpA did not interfere with either secretion of EtpA or with binding to flagellin (FIG. 6B), suggesting that the 5' end of etpA encodes domains essential for secretion (similar to other TPS molecules) and for flagellin binding. Further analysis of in-frame mutations mapping to this region led to the identification of a secreted EtpA mutant molecule with a linker insertion beginning at residue $Q_{414}$ of EtpA that had lost the capacity to bind flagellin (FIG. 6C). Compared to the wild type etpA gene, the mutant allele failed to complement the in vitro adherence defect in an isogenic etpA deletion strain jf1668 (pJMF1087) (FIG. 6D) or when the mutated protein (EtpA$_{Q414}$) was added exogenously to this mutant, jf1668 (FIG. 6E).

Figure 6F:
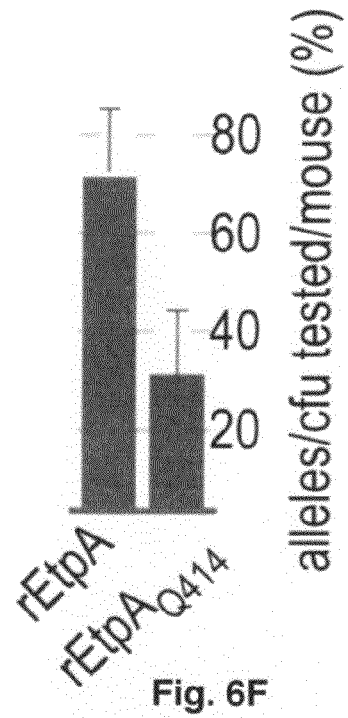

Other studies demonstrate that EtpA is required for optimal colonization of the intestine by ETEC. Likewise, jf1668 (pJMF1087) was not able to compete efficiently in intestinal colonization with the same mutant complemented with the WT etpA gene, jf1668(pJL017) (FIG. 6F), suggesting that the association of EtpA and flagellin is critical for efficient interaction of ETEC with target host cells and for colonization of mucosal surfaces.

Interestingly, previous studies demonstrated that EtpA or EtpA-like molecules are present in many ETEC strains from multiple flagellar serotypes, suggesting that this interaction between EtpA and flagellin is not limited to a small subset of ETEC strains. Likewise, BLAST searches of EtpA revealed the presence of many potential EtpA homologues in a variety of other motile gram-negative pathogens (Stover et al., 2000; Aoki et al., 2005; Welch et al., 2002; Nelson et al., 2001; Brown et al., 2004; Hochhut et al., 2006; Chen et al., 2006; Table 3), raising the possibility that other molecules could function in a similar fashion and offering a novel paradigm for the study of bacterial adhesion.

TABLE 3

EtpA homologues in flagellated organisms
EtpA homologues*: known or putative TpsA proteins† (lacking C-terminal cysteine residues) encoded flagellated human pathogens

| Accession number | organism | % identity | % similar | score |
| --- | --- | --- | --- | --- |
| ZP_00794439 | *Yersinia pseudotuberculosis* IP 31758 | 44 | 60 | 2e-120 |
| NP_253231 | *Pseudomonas aeruginosa* PAO1 | 31 | 43 | 8e-55 |
| AAG07929 | | 31 | 43 | 8e-55 |
| AAG07469 | | 41 | 57 | 7e-53 |
| NP_252771 | | 41 | 57 | 7e-53 |
| ZP_01363794 | *Pseudomonas aeruginosa* PACS2 | 31 | 46 | 3e-54 |
| ZP_01367514 | | 40 | 56 | 2e-53 |

TABLE 3-continued

EtpA homologues in flagellated organisms
EtpA homologues*: known or putative TpsA proteins† (lacking C-
terminal cysteine residues) encoded flagellated human pathogens

| Accession number | organism | % identity | % similar | score |
| --- | --- | --- | --- | --- |
| ZP_01295999 | Pseudomonas aeruginosa PA7 | 40 | 57 | 3e−56 |
| ZP_01296804 | | 44 | 61 | 3e−58 |
| ZP 01297404 | | 41 | 57 | 3e−55 |
| ZP_1298008 | | 25 | 39 | 2e−15 |
| ZP_00138031 | Pseudomonas aeruginosa UCBPP- | 31 | 44 | 3e−55 |
| ZP_00137527 | PA14 | 40 | 56 | 3e−53 |
| ZP 00138284 | | 32 | 45 | 5e−15 |
| ZP_00965590 | Pseudomonas aeruginosa C3719 | 31 | 44 | 5e−54 |
| ZP_00967564 | | 41 | 57 | 2e−53 |
| ZP_00971001 | Pseudomonas aeruginosa 2192 | 30 | 43 | 3e−55 |
| ZP_00973255 | | 40 | 55 | 7e−53 |
| ZP 00977642 | Burkholderia cenocepacia PC184 | 26 | 42 | 3e−71 |
| ZP_00983072 | Burkholderia dolosa AUO158 | 43 | 60 | 2e−44 |
| YP_773181 | Burkholderia cepacia AMMD | 41 | 59 | 3e−35 |
| ZP 00725946 | Escherichia coli F11 | 21 | 40 | 4e−12 |
| YP 672417 | Escherichia coli 536 | 21 | 40 | 1e−11 |
| YP_543880 | Escherichia coli UT189 | 22 | 40 | 2e−11 |
| AAZ57198 | Escherichia coli EC93 | 22 | 39 | 3e−08 |
| AAN78830 | Escherichia coli CFT073 | 21 | 37 | 6e−06 |
| ZP_00794439 | Yersinia pseudotuberculosis IP 31758 | 30 | 48 | 1e−110 |
| YP_001007402.1 | Yersinia enterocolitica | 43 | 59 | 2E−113 |
| AAK77860 | | 30 | 46 | 5e−104 |
| ZP_01295498 | Pseudomonas aeruginosa PA7 | 28 | 42 | 1e−35 |
| ZP_00138181 | Pseudomonas aeruginosa UCBPP-PA14 | 35 | 50 | 2e−35 |
| ZP_00971414 | Pseudomonas aeruginosa 2192 | 35 | 50 | 2e−35 |
| NP_253315 | Pseudomonas aeruinosa PA01 | 35 | 50 | 2e−35 |
| ZP_01363628 | Pseudomonas aeruinosa PACS2 | 35 | 50 | 5e−35 |
| AAO19442 | Burkholderia pseudomallei | 33 | 51 | 3e−12 |
| ZP_00464842 | Burkholderia cenocepacia H12424 | 23 | 36 | 2e−04 |
| YP_443237 | Burkholderia thailandensis E264 | 21 | 38 | 3e−04 |

*BLAST P;
†[COG3210: (Large exoproteins involved in heme utilization or adhesion)] domain.

Example 24

Targeting Conserved Regions of Flagellin Inhibits ETEC Colonization

Figure 7A:
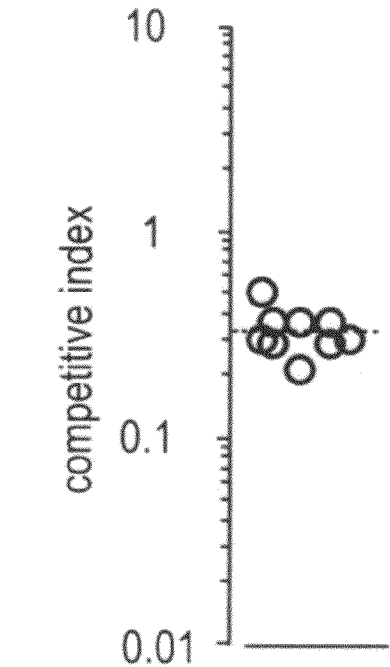
FIGS. 7A-7E show that targeting of conserved regions of flagellin inhibits ETEC infection in mice.

Recent studies demonstrated that EtpA is essential for colonization by ETEC and that EtpA serves as a protective antigen in mice. Similar to other enteric pathogens (Ottemann and Miller, 1997), it was observed that production of intact flagella was also required for efficient intestinal colonization by ETEC (FIG. 7A). Given the critical nature of EtpA interactions with conserved regions of flagellin in promoting adherence and colonization, whether immunization of mice with a single H serotype of flagellin could target shared regions of the flagellins and thereby afford heterologous protection against intestinal colonization was examined.

Figure 7B:
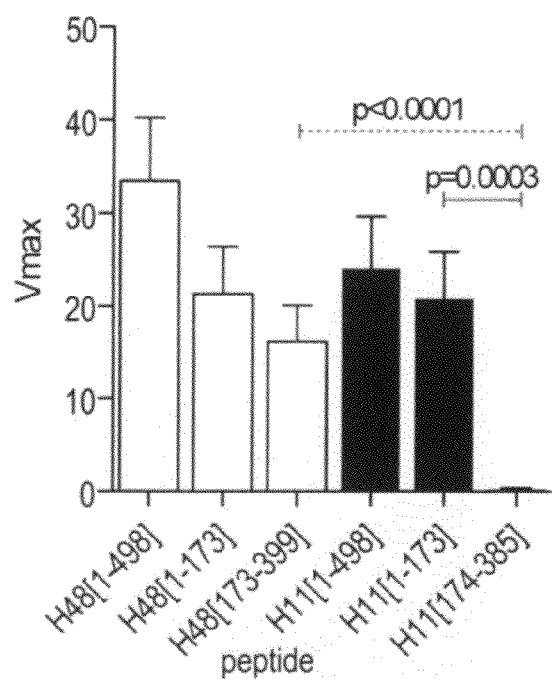
Figure 7C:
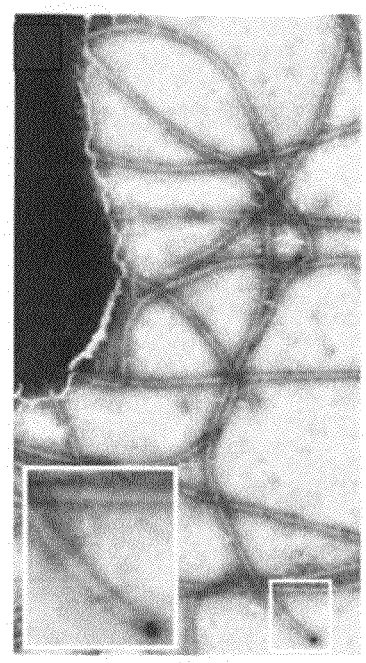
Figure 7D:
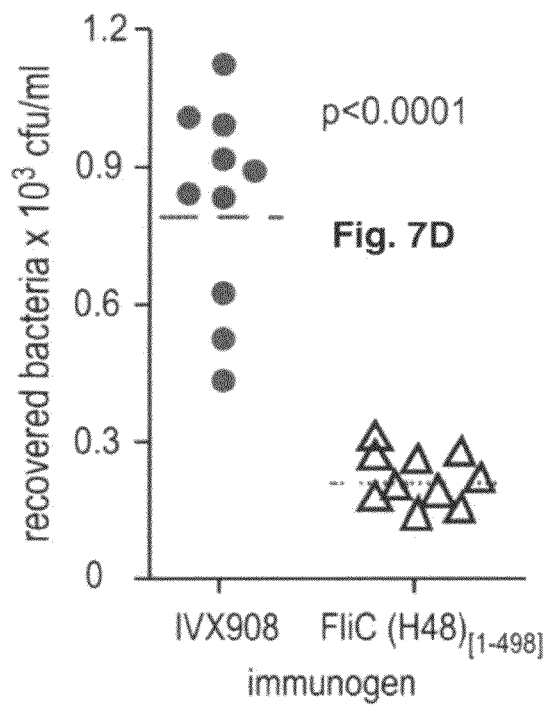
Figure 7E:
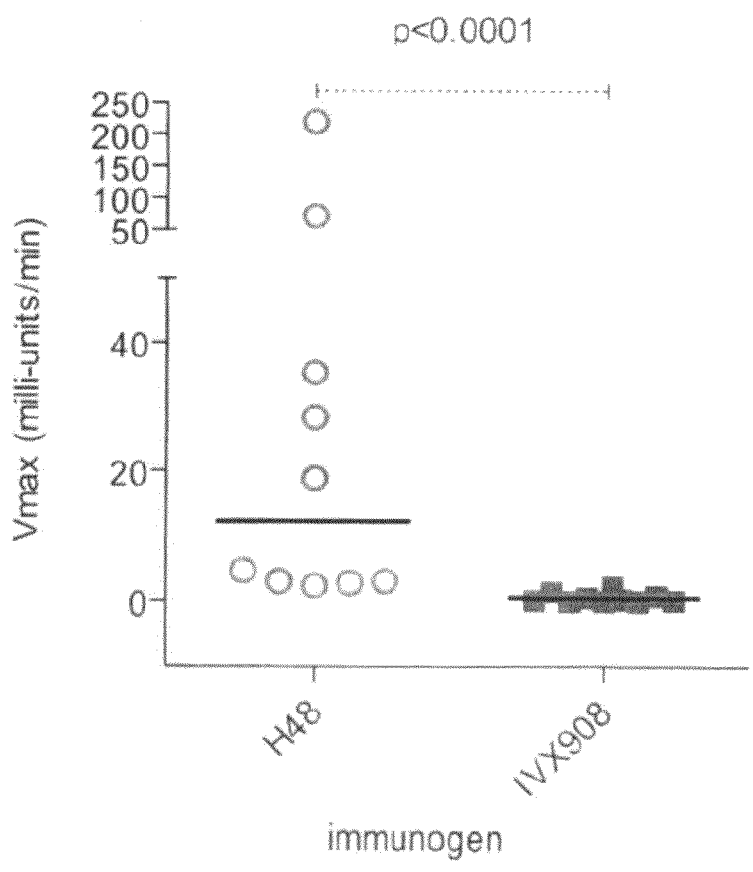

It was observed that immunization with full-length flagellin (H48) stimulated production of antibodies that recognized conserved regions of flagellin (FIG. 7B), accessible tips of H11 flagella (FIG. 7C) and inhibited colonization of ETEC expressing the heterologous flagellin H11 serotype (FIG. 7D), further suggesting that conserved regions of these molecules might present viable targets in strategies to prevent diseases caused by these pathogens. Furthermore, mice immunized intranasally with FliC$_{H48}$ developed significant fecal antibody responses directed against conserved regions of flagellin relative to IVX908 adjuvant only controls (FIG. 7E; p<0.0001).

Example 25

Bacterial Strains

ETEC strain H10407 is a fully virulent human isolate originally isolated from a child with severe diarrheal illness in Bangladesh (Evans et al., 1975). This strain, serotype O78:H11, produces heat-labile toxin (LT), heat stable toxin (ST), CFAI, as well as the recently identified enterotoxigenic Escherichia coli two-partner secretion system (Fleckenstein e al., 2006). H10407S is a spontaneous streptomycin resistant mutant of the wild type (WT). jf1289 is an isogenic etpA deletion mutant constructed from H104075 as previously described (Fleckenstein et al., 2006). AAEC191A used as a control in these studies is an afimbriate avirulent laboratory isolated derived from E. coli K-12 (Blomfield et al., 1991).

Example 26

Preparation and Administration of Immunogens

Recombinant polyhistidine tagged EtpA (rEtpA) was prepared by nickel affinity chromatography in the presence of 8 M urea as previously described (Fleckenstein et al., 2006). Urea was subsequently removed by sequential dialysis against 2M, 1M and 0.5M urea in PBS (pH 7.4). This rEtpA molecule represents approximately the first 110 kD of the mature EtpA molecule (≈170 kD), and unlike the native molecule, it is not glycosylated. IVX908 (Protillin, ID Biomedical) was supplied by the laboratory of Dr. James Dale. After anesthetizing mice with isofluorane, mice were immunized with either 7.5 µg of IVX908 alone or IVX908 (7.5 µg) with rEtpA 30 µg in a total volume of 20 µl (10 µl/nostril).

Example 27

Mouse Challenge Studies

Bacteria were prepared for mouse challenge experiments as previously described (Allen et al., 2006). Briefly, bacteria were grown overnight from frozen glycerol stocks in 2 ml cultures of Luria broth (LB) at 37° C., 250 rpm. On the morning of the challenge cultures were diluted 1:100 in side-arm flasks containing 100 ml of LB and incubated until the $OD_{600}$ reached approximately 0.14. 40 ml of the resulting culture was then centrifuged at 4° C., 10,000 rpm for 10 minutes, the supernatant discarded, and the resulting pellet resuspended in 1.6 ml of sterile PBS to achieve a bacterial concentration of approximately $1 \times 10^9$ cfu/ml. Bacteria were further diluted to in PBS achieve the final desired inoculum in 400 µl. Actual inocula were determined by plating serial dilutions of this final suspension onto Luria agar plates. For each challenge mice were pretreated with streptomycin and cimetidine to facilitate colonization (Allen et al., 2006).

In repeated exposures to either AAEC191A or H10407, mice were prepared as above followed by the administration of approximately $1 \times 10^7$ cfu of bacteria by gavage. After exposure the mice were returned to their respective cages and permitted immediate access to food and water until the next administration of bacteria. Prior to the $1^{st}$ administration of bacteria, baseline fecal pellets, and blood were obtained. Bacteria were administered on days 0, 14, 68. Fecal and blood samples were obtained again on day 95, and then 4-5 mice from each group were challenged with either $6 \times 10^7$ or $6 \times 10^3$ cfu of WT H10407.

Example 28

Immunoassays

Blood was obtained from mice by periorbital bleeding using capillary tubes or by intracardiac puncture on sacrifice of the animals following challenge. After clotting, serum was centrifuged briefly to remove remaining cells and transferred to fresh tubes and stored at –80° C. for subsequent assay. To obtain fecal antibodies, 5 fresh pellets were obtained for each animal. These were placed immediately into 1.5 ml fecal reconstitution buffer (FRS) containing Tris (10 mM), NaCl (100 mM), Tween-20 (0.05%) and sodium azide (5 mM) at pH 7.4. Samples were vortexed to homogeneity, and spun at 1500×g at 4° C. for 10 minutes to remove insoluble material. Supernatants were saved and stored at –80° C. for subsequent analysis.

Purified rEtpA and rEtpB, prepared by nickel affinity chromatography, were diluted in 0.1 M $NaHCO_3$ buffer, pH 8.6 to a final concentration of approximately 4 µg/ml. 50 µl of each respective solution was used to coat individual wells of an ELISA plate (Immunolon, Nunc) overnight at room temperature (RT). After washing to remove excess antigen, the plate was blocked with a solution of 1% BSA (Blocker, Pierce) in PBS containing 0.05% Tween-20 (PBST) for 1 hour at RT. After removal, 50 µl of each antibody-containing solution diluted in PBST was added and incubated for 1 hour. The plate was washed with PBST, and developed with HRP-labeled goat anti-mouse (IgG, IgM, IgA) antibody followed by washing and detection with tetramethylbenzidine/$H_2O_2$ (TMB) peroxidase substrate (Kierkegaard & Perry Laboratories). Reactions were stopped after significant color development by the addition of 1M H2SO4, and the $OD_{405}$ was determined spectrophotometrically.

Example 29

Mice Repeatedly Exposed to ETEC Recognize ETEC-Specific Antigens and are Protected from Subsequent Colonization The present invention examined whether repeated exposure to enterotoxigenic *Escherichia coli* in the murine model would afford significant protection against subsequent intestinal colonization, thereby mimicking natural infections in humans. Mice were repeatedly exposed to either human enterotoxigenic *Escherichia coli* isolate H10407 which effectively colonizes murine intestines, or an avirulent non-colonizing laboratory *E. coli* strain AAEC191A. Both groups of previously exposed mice were then challenged with two different doses of ETEC H10407.

Figure 8A:
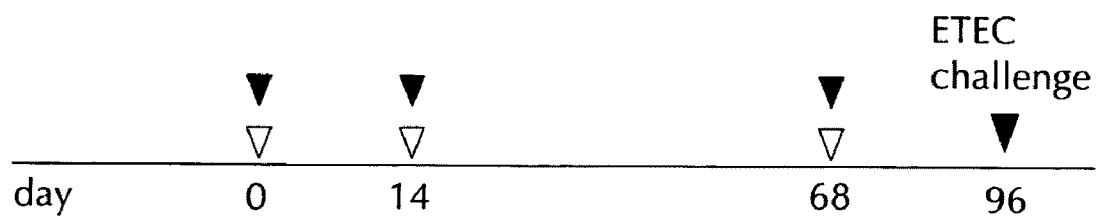
FIGS. 8A-8D show that mice repeatedly inoculated with enterotoxigenic *Escherichia coli* mount immune responses to enterotoxigenic *Escherichia coli* TPS proteins and are protected from subsequent challenge.
Figure 8B:
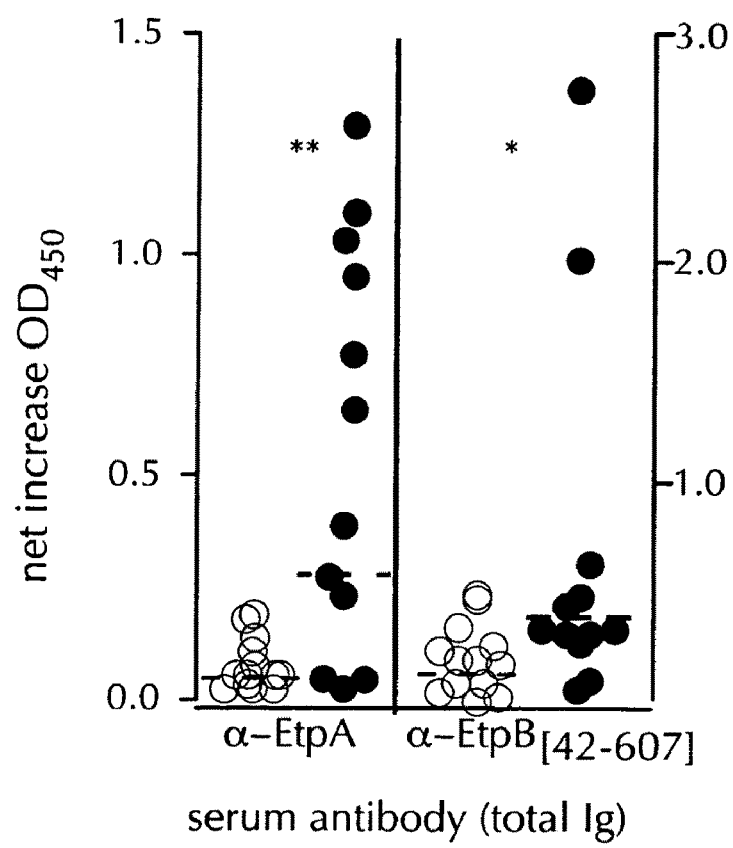

Repeated exposure to infections with enterotoxigenic *Escherichia coli* H10407 resulted in significant serum (FIG. 8A) and fecal (FIG. 8B) antibody responses to both EtpA and EtpB, components of the recently identified enterotoxigenic *Escherichia coli* two-partner secretion system. These data suggested that these proteins were expressed in vivo in this model, and that mice recognized extracellular enterotoxigenic *Escherichia coli* proteins during the course of experimental infection.

Figure 8C:
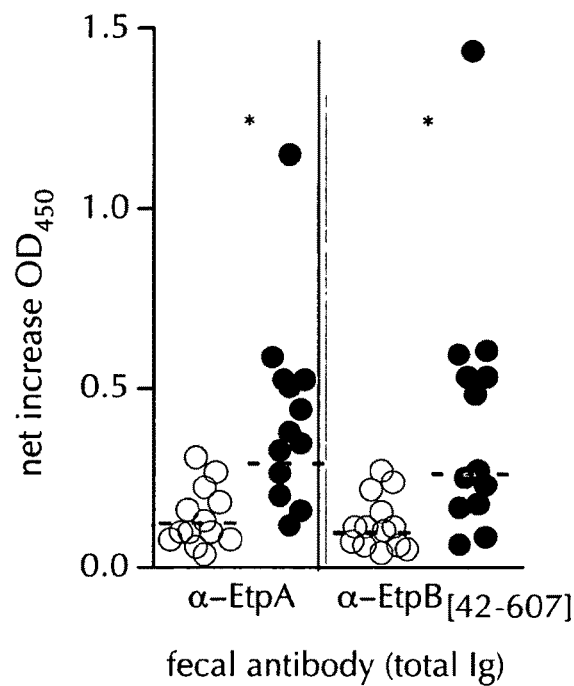
Figure 8D:
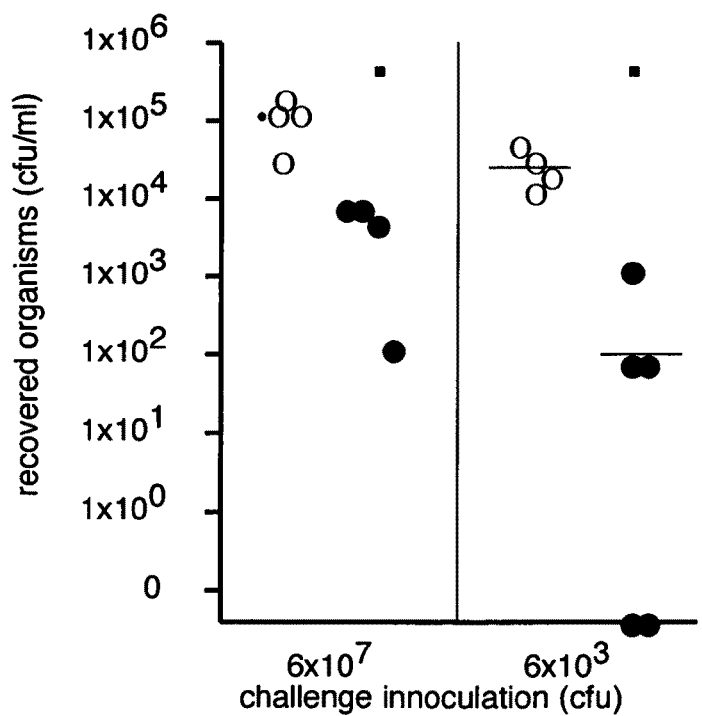

Interestingly, mice that were repeatedly exposed to enterotoxigenic *Escherichia coli* were significantly protected from subsequent intestinal colonization with H10407 when compared to those previously inoculated with the afimbriate non-colonizing AAEC191A strain (FIG. 8C). Together, these results suggested that during the course of repeated infection with enterotoxigenic *Escherichia coli*, mice in this model developed protective immune responses that were directed against enterotoxigenic *Escherichia coli*-specific antigens, and likewise that this model may be used to examine the protective efficacy of candidate immunogens.

Example 30

EtpA is Required for Optimal Colonization of Murine Intestine

EtpA is member of a family of virulence proteins (generically referred to as TpsA proteins) that are secreted by TPS. TpsA exoproteins similar to EtpA play critical roles in bacterial adhesion in vitro (Reiman et al., 1989), and in colonization of mucosal surfaces in vivo (Kimura et al., 1990). Furthermore, these proteins serve as protective antigens and have been incorporated in the development of highly effective acellular vaccines for other important mucosal pathogens such as *Bordetella pertussis* (Gustafsson et al., 1996). Therefore, additional studies were performed to examine the contribution of EtpA to colonization of the intestine, and its potential role as a protective immunogen in the experimental mouse model.

As demonstrated in FIGS. 9A-9B, the isogenic etpA mutant was deficient in colonization of murine intestine. In FIG. 9A, the y-axis shows number of CFU/ml recovered from intestinal lysates obtained approximately 24 h after challenge. In three mice challenged with jf1289 strain, no organisms were recovered from intestinal lysates and these are arbitrarily represented at the theoretical limit of detection (1 CFU on the graph). The dashed horizontal lines for each data set indicate the respective geometric mean values. P=0.001 by two tailed Mann-Whitney analysis.

In FIG. 9B, each point on the graph represents the CI calculated from a single mouse. To calculate the CI, the ratio of vector colonies (jf1668 complemented with vector only) compared to recombinant colonies (jf 1668 complemented with the pJL017 EtpA expression plasmid) first determined by PCR of Cmr Ampr colonies grown from intestinal lysates (i.e., [vector/recombinant]output PCR). An average of nine Cmr Ampr colonies were tested per each mouse. This ratio was then divided by the ratio of vector to recombinant-complemented colonies present in the initial inoculum as determined by plating dilutions of each strain (i.e., [vector/recombinant]input CFU). One mouse was colonized with jf1668(pJY017), but no jf1668(pBADmyc/HisA) were identified by PCR, and this mouse is represented as a CI of 0.07 on the graph, indicating the limits of detection for this assay. The dashed horizontal line represents the geometric mean CI (0.19), implying that on average the strain complemented with the EtpA expression plasmid was 5-fold more fit for colonization than that complemented with the vector alone under these conditions. P 0.0062 by Mann-Whitney (two-tailed) testing of the two groups. Graph inset was obtained by anti-EtpA immunoblotting of trichloroacetic acid-precipitated supernatants of jf1668 complemented with either pJL017 (shown on left) or vector control pBADmycHisA (shown on right) after induction with 0.0002% arabinose.

Example 31

Immunogenicity and Protective Efficacy of EtpA

Figure 10A:
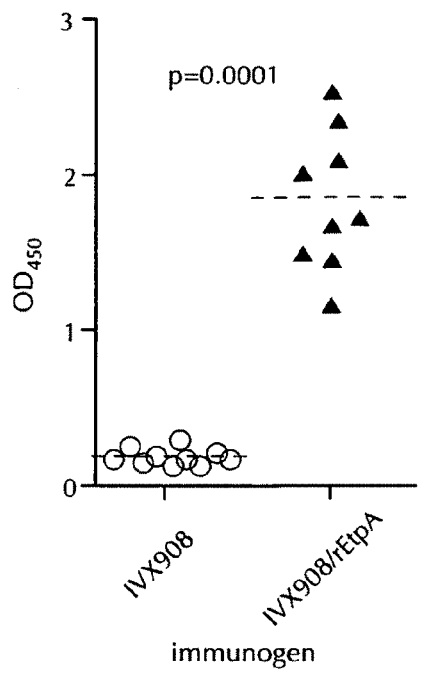
FIGS. 10A-10D show immunogenicity and protective efficacy of recombinant EtpA tested in a murine model of enterotoxigenic *Escherichia coli* colonization. Mice immunized intranasally with either IVX908 alone (controls) or IVX908+ recombinant, non glycosylated polyhistidine-tagged EtpA (30 µg/dose) on days 0, 22, 42. On day 63 mice were given 8.5×10$^4$ cfu of WT ETEC (H10407) by oral gavage, and the degree of colonization was assessed approximately 24 hours after inoculation.
Figure 10B:
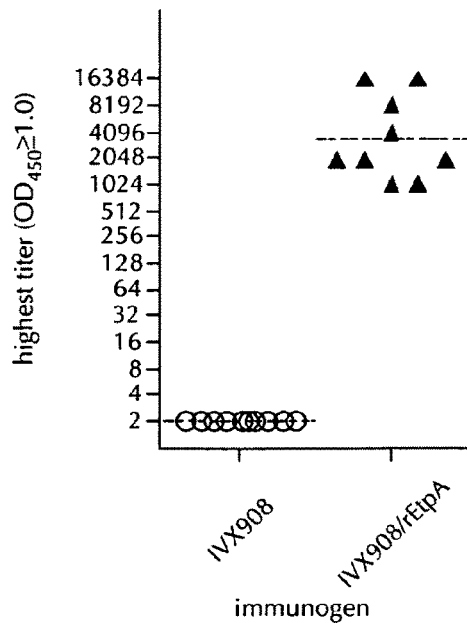
Figure 10C:
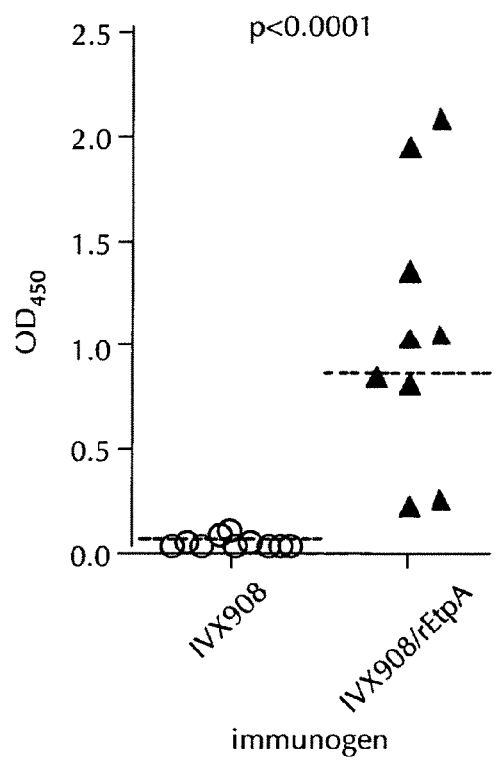

Next, mice were immunized with either a proteosome/LPS-based mucosal adjuvant, IVX908 or IVX908+recombinant EtpA. When administered intranasally, the IVX908/rEtpA formulation was highly immunogenic (FIG. 10A), resulting in high-titer ($\geq$1:1024) serologic responses in each of the immunized mice (FIG. 10B) Significant responses to EtpA were also detected in saliva (FIG. 10C). However, significant increases in fecal antibody in EtpA vaccinated-mice relative to controls were not observed (not shown).

Figure 10D:
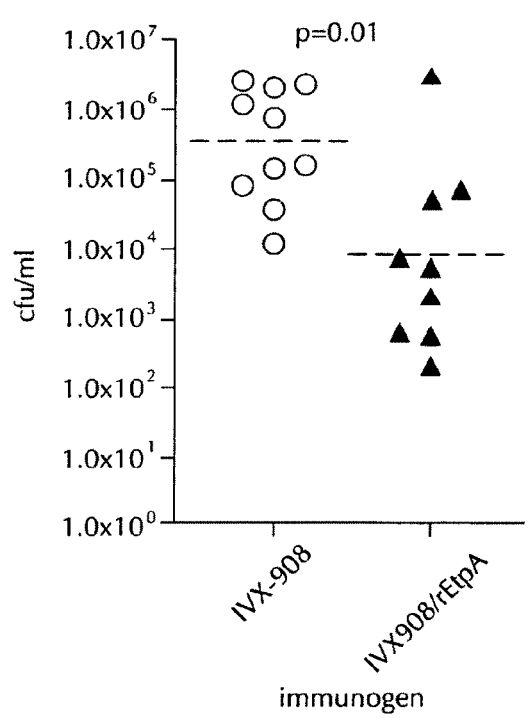

Mice that had been immunized in this fashion with $\approx 8 \times 10^4$ cfu of wild type enterotoxigenic *Escherichia coli* H10407 were then challenged. As shown in FIG. 10D, mice immunized in this fashion were afforded significant protection from enterotoxigenic *Escherichia coli* colonization relative to controls.

The following references were cited herein:
Allen, et al., *Infect Immun* 74, 869-75 (2006).
Aoki et al., Science 309(5738), 1245 (2005).
Altschul et al., *Nucleic Acids Res* 25, 3389-402 (1997).
Beatty et al. Clin Infect Dis 42:329-34 (2006)
Blattner. et al. *Science* 277, 1453-74 (1997).
Blomfield et al., *Mol Microbiol* 5:1447-57 (1991).
Boedeker, *Curr Opin Gastroenterol* 21, 15-9 (2005).
Bourgeois et al. *Am J Trop Med Hyg* 48:243-8 (1993)
Brandtzaeg P. Vaccine 2006
Brown et al., Mol Genet Genomics 272(2), 204 (2004).
Buscher et al., *Mol Microbiol* 2006
Chen et al, Proc Natl Acad Sci USA 103(15), 5977 (2006).
Chenna, et al. *Nucleic Acids Res* 31, 3497-500 (2003).
Clemens, et al. *J Infect Dis* 158, 372-7 (1988).
Correa et al., *Mol Microbiol* 35, 743-55 (2000).
Coster et al. *Infect Immun;* 75:252-9 (2007)
Daniels, *Clin Infect Dis* 42:335-6 (2006).
Datsenko, & Wanner, *Proc Natl Acad Sci USA* 97, 6640-5 (2000).
Doring et al., Proc Natl Acad Sci USA 104(26), 11020 (2007).
Dorsey et al., *Cellular Microbiology* 8, 1516-1527 (2006).
Elsinghorst & Kopecko, *Infect Immun* 60, 2409-17 (1992).
Evans and Evans *Infect Immun* 8:322-8 (1973).
Evans et al., *Infect Immun* 12, 656-67 (1975).
Fleckenstein et al., *Infect Immun* 74, 2245-58 (2006).
Giron et al., *Mol Microbiol* 44, 361-79 (2002).
Goff and Prasad, Methods Enzymol 208, 586 (1991).
Golemis and Adams, Protein-protein interactions: a molecular cloning manual, $2^{nd}$ ed (Cold spring Harbor Laboratory Press, Cold Spring Harbor, N.Y., 2005)
Gustafsson et al., *N Engl J Med* 334:349-55 (1996).
Harlow, et al., *Using antibodies: a laboratory manual*, xiv, 495 p. (Cold Spring Harbor Laboratory Press, Cold Spring Harbor, N.Y., 1999).
Hayashi, et al., *Nature* 410, 1099-103 (2001).
Hochhut et al., Mol Microbiol 61(3), 584 (2006).
Holmgren and Czerkinsky, *Nat Med* 11:S45-53 (2005).
Hyams et al. *N Engl J Med,* 325:1423-8 (1991)
Jacob-Dubuisson et al., *Mol Microbiol* 40, 306-13 (2001).
Jiang et al. *J Infect Dis* 185:497-502 (2002).
Kimura et al., *Infect Immun* 58:7-16 (1990).
Kirn and Taylor *Infect Immun* 73:4461-70 (2005).
Komoriya, et al. *Mol Microbiol* 34, 767-79 (1999).
Kosek et al., *Bull World Health Organ* 81, 197-204 (2003).
Lane, et al. *Infect Immun* 73, 7644-56 (2005).
Lee et al. *Infect Immun;* 67:5799-805 (1999).
Levine et al., *Infect Immun;* 23:729-36 (1979).
Lindenthal, & Elsinghorst, *Infect Immun* 69, 52-7 (2001).
Lin et al. *N Engl J Med* 344:1263-9 (2001)
Majander, et al. *Nat Biotechnol* 23, 475-81 (2005).
Maloy et al., in Genetic analysis of pathogenic bacteriaL a laboratory manual (Cold Spring Harbor Laboratory Press, Cold Spring Harbor, N.Y., 1996), Vol. 1, pp. 49.
Moreland et al., *BMC Bioinformatics* 6, 21 (2005).
Nelson et al., Infect Immunol 69(10), 6201 (2001).
Ofek et al., *Bacterial adhesion to animal cells and tissues*, x, 416 p. (ASM Press, Washington, D.C., 2003).
Otemann and Miller, Mol Microbiol, 24(6), 1109 (1997).
Peruski. et al. *J. Clin. Microbiol.* 37, 2974-2978 (1999).
Pratt & Kolter, *Mol Microbiol* 30, 285-93 (1998).
Relman et al., *Proc Natl Acad Sci USA* 86:2637-41 (1989)
Sack. et al. *J Infect Dis* 123, 378-85 (1971).
Sack, *Rev Inf Dis;* 12:S59-S63 (1990)
Simons et al., *Gene* 53: 85-96.
Smith, et al. *Nat Immunol* 4, 1247-53 (2003).
Steinsland et al., *Lancet* 362:286-91 (2003).
Stover et al., *Nature* 406 (6799), 959 (2000).
Subramanian & Qadri, *Nat Immunol* 7, 583-9 (2006).
Vicente et al. *Trans R Soc Trop Med Hyg* 99, 669-74 (2005).
Walker et al., Vaccine 2006
Welch et al., Proc Natl Acad Sci USA 99(26), 17020 (2002).
WHO. *Wkly Epidemiol Rec* 81, 97-104 (2006).
Wolf, *Clin Microbiol Rev* 10, 569-84 (1997).
Wright et al., *Infect Immun* 73, 7657-68 (2005).
Yao. et al. *Mol Microbiol* 14, 883-93 (1994).
Yonekura, et al, Science 290, 2148-52 (2000).
Yonekura et al., *Nature* 424, 643-50 (2003).

What is claimed is:

1. An immunogenic composition, comprising:
   EtpA and
   a pharmaceutically acceptable adjuvant.

2. The immunogenic composition of claim 1, wherein the EtpA is a recombinant protein.

3. The immunogenic composition of claim 2, wherein the recombinant protein is produced in *Escherichia coli* or an attenuated bacterial pathogen.

4. The immunogenic composition of claim 2, wherein the recombinant protein comprises modified or unmodified amino acids.

5. A method of inducing an antibody response to an enterotoxigenic *Escherichia coli* infection in an individual, comprising: administering an immunologically effective amount of the immunogenic composition of claim 1 to said individual.

6. The method of claim 5, wherein the individual is a healthy individual, is at high risk of developing the infection or has been exposed to the enterotoxigenic *Escherichia coli*.

7. The method of claim 5, wherein the immunogenic composition is administered sub-cutaneously, intramuscularly, intranasally or mucosally.

8. The immunogenic composition of claim 1, further comprising a flagellin protein.

9. The immunogenic composition of claim 8, wherein said flagellin protein is derived from *Escherichia coli* serotype H48.

* * * * *